United States Patent
Mendell et al.

(10) Patent No.: US 10,842,886 B2
(45) Date of Patent: Nov. 24, 2020

(54) GUIDED INJECTIONS FOR AAV GENE TRANSFER TO MUSCLE

(71) Applicant: RESEARCH INSTITUTE AT NATIONWIDE CHILDREN'S HOSPITAL, Columbus, OH (US)

(72) Inventors: Jerry R. Mendell, Columbus, OH (US); Brian K. Kaspar, Westerville, OH (US); Samiah Al-Zaidy, Columbus, OH (US)

(73) Assignee: RESEARCH INSTITUTE AT NATIONWIDE CHILDREN'S HOSPITAL, Columbus, OH (US)

(*) Notice: Subject to any disclaimer, the term of this patent is extended or adjusted under 35 U.S.C. 154(b) by 0 days.

(21) Appl. No.: 15/517,623

(22) PCT Filed: Oct. 9, 2015

(86) PCT No.: PCT/US2015/055022
§ 371 (c)(1),
(2) Date: Apr. 7, 2017

(87) PCT Pub. No.: WO2016/057975
PCT Pub. Date: Apr. 14, 2016

(65) Prior Publication Data
US 2017/0246322 A1 Aug. 31, 2017

Related U.S. Application Data

(60) Provisional application No. 62/062,592, filed on Oct. 10, 2014.

(51) Int. Cl.
| | | |
|---|---|---|
| *A61K 48/00* | (2006.01) | |
| *A61K 39/23* | (2006.01) | |
| *C12N 15/86* | (2006.01) | |
| *C07H 21/04* | (2006.01) | |
| *A61K 38/17* | (2006.01) | |
| *C07K 14/47* | (2006.01) | |
| *C12N 7/00* | (2006.01) | |

(52) U.S. Cl.
CPC ...... *A61K 48/0075* (2013.01); *A61K 38/1709* (2013.01); *A61K 48/00* (2013.01); *C07K 14/4703* (2013.01); *C12N 7/00* (2013.01); *C12N 15/86* (2013.01); *C07H 21/04* (2013.01); *C12N 2750/14142* (2013.01); *C12N 2750/14143* (2013.01); *C12N 2750/14171* (2013.01); *C12N 2799/025* (2013.01)

(58) Field of Classification Search
CPC .............. A61K 48/005; C12N 15/8645; C12N 2750/14142; C12N 2750/14143; C07H 21/04
USPC .................. 514/44 R; 435/320.1; 424/233.1; 536/23.5
See application file for complete search history.

(56) References Cited

U.S. PATENT DOCUMENTS

| | | | |
|---|---|---|---|
| 5,173,414 | A | 12/1992 | Lebkowski et al. |
| 5,658,776 | A | 8/1997 | Flotte et al. |
| 5,786,211 | A | 7/1998 | Johnson |
| 5,871,982 | A | 2/1999 | Wilson et al. |
| 6,258,595 | B1 | 7/2001 | Gao et al. |
| 6,566,118 | B1 | 5/2003 | Atkinson et al. |
| 2011/0112067 | A1* | 5/2011 | Hartmann et al. |
| 2014/0171918 | A1* | 6/2014 | Logomasini |

FOREIGN PATENT DOCUMENTS

| | | |
|---|---|---|
| WO | WO-95/13365 A1 | 5/1995 |
| WO | WO-95/13392 A1 | 5/1995 |
| WO | WO-96/17947 A1 | 6/1996 |
| WO | WO-97/06243 A1 | 2/1997 |
| WO | WO-97/08298 A1 | 3/1997 |
| WO | WO-97/09441 A2 | 3/1997 |
| WO | WO-97/21825 A1 | 6/1997 |
| WO | WO-98/09657 A3 | 4/1998 |
| WO | WO-99/11764 A3 | 6/1999 |
| WO | WO-01/83692 A3 | 3/2002 |
| WO | WO-02/053703 A2 | 7/2002 |
| WO | WO-2008/067480 A2 | 6/2008 |

OTHER PUBLICATIONS

Aartsma-Rus et al., Theoretic applicability of antisense-mediated exon skipping for Duchenne muscular dystrophy mutations. *Hum. Mutat.*, 30:293-9 (2009).
Amthor et al., Follistatin complexes Myostatin and antagonises Myostatin-mediated inhibition of myogenesis, *Developmental Biol.*, 270:19-30 (2004).
Aoki et al., Attenuation of bleomycin-induced pulmonary fibrosis by follistatin. *Am. J. Respir. Crit. Care. Med.*, 172:713-20 (2005).
Aroua et al., Pituitary gonadotropins FSH and LH are oppositely regulated by the activin/follistatin system in a basal teleost, the eel. *Gen. Comp. Endocrinol.*, 175:82-91 (2011).
Azam et al., Anticipating Clinical resistance to target-directed agents: the BCR-ABL paradigm, *Mol. Ther.*, 13(1): 67-76 (2006).
Backman et al., Low-dose prednisolone treatment in Duchenne and Becker muscular dystrophy. *Neuromuscul. Disord.*, 5:233-41(1995).
Beggs et al., Exploring the molecular basis for variability among subjects with Becker muscular dystrophy: dystrophin gene and protein studies. *Am. J. Hum. Genet.*, 49:54-67 (1991).

(Continued)

*Primary Examiner* — Shin Lin Chen
(74) *Attorney, Agent, or Firm* — Marshall, Gerstein & Borun LLP

(57) ABSTRACT

The disclosure relates to methods for treating subjects with musculoskeletal diseases or with muscle wasting not associated with a musculoskeletal disease by gene transfer with recombinant adeno-associated viruses (rAAV) encoding myostatin inhibitors such as follistatin-344. The rAAV are administered prior to development of diffuse muscle fibrosis in a subject, or the rAAV administration avoids regions of muscle fibrosis in a subject.

9 Claims, 18 Drawing Sheets
Specification includes a Sequence Listing.

(56) References Cited

OTHER PUBLICATIONS

Bogdanovich et al., Functional improvement of dystrophic muscle by myostatin blockade. *Nature*, 420: 418-21 (2002).
Bogdanovich et al., Myostatin propeptide-mediated ameliortion of dystophic pathophysiology, *FASEB J.*, 19: 543-9 (2005).
Brooke et al., Clinical investigation in Duchenne Dystrophy. II. Determination of the "power" of therapeutic trials based on the natural history. *Muscle Nerve*, 6:91-103 (1983).
Bushby et al., The clinical, genetic and dystrophin characteristics of Becker muscular dystrophy. II. Correlation of phenotype with genetic and protein abnormalities. *J. Neurol.*, 240:105-12 (1993).
Bushby et al., The clinical, genetic and dystrophin characteristics of Becker muscular dystrophy. I. Natural History. *J Neurol.* 240:98-104 (1993).
Carter, Adeno-associated virus vectors, *Curr. Opin. in Biotechnol.*, 3:533-9 (1992).
Chandrasekharan et al., Genetic defects in muscular dystrophy. *Methods Enzymol.*, 479: 291-322 (2010).
Chao et al., Several Log Increase in Therapeutic Transgene Delivery by Distinct Adeno-associated Viral Serotype Vectors, *Mol. Ther.*, 2:619-23 (2000).
Chao et al., Sustained and complete phenotype correction of hemophilia B mice following intramuscular injection of AAV1 serotype vectors, *Mol. Ther.*, 4:217-22 (2001).
Clark et al., A stable cell line carrying adenovirus-inducible rep and cap genes allows for infectivity titration of adeno-associated virus vectors. *Gene Therapy*, 3:1124-32 (1996).
Clark et al., Highly purified recombinant adeno-associated virus vectors are biologically active and free of detectable helper and wild-type viruses, *Hum. Gene Ther.*, 10:1031-9 (1999).
Clark et al., Recombinant Adeno-Associated Viral Vectors Mediate Long-Term Transgene Expression in Muscle, *Hum Gene Ther.*, 8:659-69 (1997).
Clop et al., A mutation creating a potential illegitimate microRNA target site in the myostatin gene affects muscularity in sheep. *Nature Genet.*, 38:813-18 (2006).
Cserjesi et al., Myogenin induces the myocyte-specific enhancer binding factor MEF-2 independently of other muscle-specific gene products, *Mol. Cell. Biol.*, 11:4854-62 (1990).
England et al., Very mild muscular dystrophy associated with the deletion of 46% of dystrophin. *Nature*, 343:180-2 (1990).
Flanigan et al., Mutational spectrum of DMD mutations in dystrophinopathy subjects: application of modern diagnostic techniques to a large cohort, *Hum. Mutat.*, 30:1657-56 (2009).
Flanigan et al., Nonsense mutation-associated Becker muscular dystrophy: interplay between exon definition and splicing regulatory elements within the DMD gene, *Hum. Mutat.*, 32:299-308 (2011).
Forbes et al., Skeletal muscles of ambulant children with Duchenne muscular dystrophy: validation of multicenter study of evaluation with MR imaging and MR spectroscopy, *Radiology*, 269(1):198-207 (2013).
Gao et al., Clades of Adeno-associated viruses are widely disseminated in human tissues. *J. Virol.*, 78: 6381-88 (2004).
GenBank Accession No. AF085716, Adeno-associated virus 5 DNA binding trs helicase (Rep22) and capsid protein (VP1) genes, complete cds, Feb. 9, 1999.
GenBank Accession No. AX753246, Sequence 1 from Patent EP1310571, Jun. 23, 2003.
GenBank Accession No. AX753249, Sequence 4 from Patent EP1310571, Jun. 23, 2003.
GenBank Accession No. NC_001829, Adeno-associated virus—4, complete genome, Jan. 28, 2010.
GenBank Accession No. NC_002077, Adeno-associated virus—1, complete genome, Mar. 11, 2010.
GenBank Accession No. NC001401, Adeno-associated virus—2, complete genome, Dec. 2, 2014.
GenBank Accession No. NC001862, *Homo sapiens* cytochrome c oxidase subunit 5B (COX5B), mRNA, Oct. 1, 2017.
Genbank Accession No. NM 013409, *Homo sapiens* follistatin (FST), transcript variant FST344, mRNA, Oct. 9, 2017.
Gilson et al., Follistatin induces muscle hypertrophy through satellite cell proliferation and inhibition of both myostatin and activin. *Am. J. Physiol. Endocrinol. Metab.*, 297:E157-64 (2009).
Govoni et al., Ongoing therapeutic trials and outcome measures for Duchenne muscular dystrophy. *Cell Mol. Life Sci.*, 70(23):4585-602 (2013).
Grobet et al., A deletion in the bovine myostatin gene causes the double-muscled phenotype in cattle, *Nat. Genet.*, 17:71-4 (1997).
Haidet et al., Long-term enhancement of skeletal muscle mass and strength by single gene administration of myostatin inhibitors, *Proc. Natl. Acad. Sci. USA.*, 105:4318-22 (2008).
Hawley et al., Computed tomographic patterns of muscles in neuromuscular diseases. *Arch. Neurol.*, 41:383-87 (1984).
Hermonat et al., Use of adeno-associated virus as a mammalian DNA cloning vector: transduction of neomycin resistance into mammalian tissue culture cells. *Proc. Natl. Acad. Sci. USA*, 81:6466 (1984).
Herzog et al., Stable gene transfer and expression of human blood coagulation factor IX after intramuscular injection of recombinant adeno-associated virus. *Proc. Natl. Acad. Sci. USA*, 94:5804-9 (1997).
Hill et al., The myostatin propeptide and the follistatin-related gene are inhibitory binding proteins of myostatin in normal serum. *J. Biol. Chem.*, 277(43):40735-41 (2002).
Inouye et al., Recombinant expression of human follistatin with 315 and 288 amino acids: Chemical and biological comparison with native porcine follistatin. *Endocrinol.*, 129:815-22 (1991).
Johnson et al., Muscle creatine kinase sequence elements regulating skeletal and cardiac muscle expression in transgenic mice. *Mol. Cell. Biol.*, 9:3393-9 (1989).
Kaiser et al., Follistatin gene expression in the pituitary: localization in gonadotropes and folliculostellate cells in diestrous rats. *Endocrinology*, 130:3048-56 (1992).
Kambadur et al., Mutations in myostatin (GDF8) in double-muscled Belgian Blue and Piedmontese cattle, *Genome Res.*, 7:910-5 (1997).
Kessler et al., Gene delivery to skeletal muscle results in sustained expression and systemic delivery of a therapeutic protein, *Proc Nat. Acad Sci. USA*, 93:14082-7 (1996).
Kinali et al., Local restoration of dystrophin expression with the morpholino oligomer AVI-4658 in Duchenne muscular dystrophy: a single-blind, placebo-controlled, dose-escalation, proof-of-concept study. *Lancet Neurol.*, 8:918-28 (2009).
Kinali et al., Muscle histology vs MRI in Duchenne muscular dystrophy. *Neurology*, 76:346-53 (2011).
Kota et al., Follistatin Gene Delivery Enhances Muscle Growth and Strength in Nonhuman Primates. *Sci. Transl. Med.*, 1:6ra15 (2009).
Laughlin et al., Cloning of infectious adeno-associated virus genomes in bacterial plasmids, *Gene*, 23:65-73 (1983).
Lebkowski et al., Adeno-Associated Virus: a Vector System for Efficient Introduction and Integration of DNA into a Variety of Mammalian Cell Types, *Mol. Cell. Biol.*, 7:349 (1988).
Lee et al., Regulation of myostatin activity and muscle growth, *Proc. Natl. Acad. Sci. USA*, 98:9306-11 (2001).
Lee et al., Role of satellite cells versus myofibers in muscle hypertrophy induced by inhibition of the myostatin/activin signaling pathway, *Proc. Natl. Acad. Sci. USA*, E2353-60 (2012).
Lee, Quadrupling muscle mass in mice by targeting TGF-beta signaling pathways. *PLoS One*, 2:e789 (2007).
Lee, Regulation of muscle mass by myostatin. *Ann. Rev. Cell. Dev. Biol.*, 20:61-86 (2004).
Leung et al., Sildenafil does not improve cardiomyopathy in Duchenne/Becker muscular dystrophy. *Ann Neurol*, 76(4):541-9 (2014).
Lewis et al., Generation of neutralizing activity against human immunodeficiency virus type 1 in serum by antibody gene transfer. *J. Virol.*, 76:8769-75 (2002).
Mader et al., A steroid-inducible promoter for the controlled overexpression of cloned genes in eukaryotic cells. *Proc. Natl. Acad. Sci. USA*, 90:5603-7 (1993).
McCroskery et al., Improved muscle healing through enhanced regeneration and reduce fibrosis in myostatin null mice. *J. Cell. Sci.*, 118:3531-41 (2005).

(56) References Cited

OTHER PUBLICATIONS

McCroskery et al., Myostatin negatively regulates satellite cell activation and self-renewal. *J. Cell. Biol.*, 162:1135-47 (2003).
McDonald et al., The 6-minute walk test and other endpoints in Duchenne muscular dystrophy: Longitudinal natural history observations over 48 weeks from a multicenter study, *Muscle Nerve*. 48:343-56 (2013).
McLaughlin et al., Adeno-associated virus general transduction vectors: analysis of proviral structures, *J. Virol.*, 62:1963 (1988).
McPherron et al., Double muscling in cattle due to mutations in the myostatin gene. *Proc. Natl. Acad. Sci. USA*, 94:12457-61 (1997).
McPherron et al., Regulation of skeletal muscle mass in mice by a new TGF-beta superfamiliy member. *Nature*, 387:83-90 (1997).
Mendell et al . Eteplirsen for the treatment of Duchenne muscular dystrophy. *Ann. Neurol.*, 74:637-47 (2013).
Mendell et al., Gene Therapy for Muscular dystrophy: Lessons learned and path forward. *Neurosci. Let.*, 527(2):90-99 (2012).
Mendell et al., A phase 1/2a follistatin gene therapy tial for becker muscular dystrophy. *Molec. Ther.*, 23(1):192-201 (2015).
Mendell et al., Clinical investigation of Duchenne muscular dystrophy. A methodology for therapeutic trials based on natural history controls. *Arch Neurol.*, 44:808-11 (1987).
Mendell et al., Limb-girdle muscular dystrophy 2D gene therapy restores alpha-sarcoglycan and associated proteins. *Ann. Neurol.*, 66:290-7 (2009).
Mendell et al., Sustained Alpha-Sarcoglycan Gene Expression after Gene Transfer in Limb-Girdle Muscular Dystrophy, Type 2D. *Ann. Neurol.*, 68:629-38 (2010).
Mercuri et al., A short protocol for muscle MRI in children with muscular dystrophies. *Eur. J. Paediatric Neurology*, 6:305-7 (2002).
Mercuri et al., Clinical and imaging findings in six cases of congenital muscular dystrophy with rigid spine syndrome linked to chromosome 1p (RSMD1). *Neuromuscul. Disord.*, 12:631-8 (2002).
Mercuri et al., Muscle MRI findings in a three-generation family affected by Bethlem myopathy. *Eur. J. Paediatric Neurology*,6(6):309-14 (2002).
Michel et al., Rat follistatin: gonadal and extragonadal expression and evidence for alternative splicing. *Biochem. Biophys. Res. Commun.*, 173:401-7 (1990).
Mori et al., Two novel adeno-associated viruses from cynomolgus monkey: pseudotyping characterization of capsid protein. *Virology*, 330(2):375-83 (2004).
Mosher et al., A mutation in the myostatin gene increases muscle mass and enhances racing performance in heterozygote dogs. *PLoS Genetics*, 3:e779-86 (2007).
Murphy et al., Long-term correction of obesity and diabetes in genetically obese mice by a single intramuscular injection of recombinant adeno-associated virus encoding mouse leptin. *Proc. Natl. Acad. Sci. USA*, 94:13921-6 (1997).
Muscat et al., Multiple 5'-flanking regions of the human alpha-skeletal actin gene synergistically modulate muscle-specific expression. *Mol. Cell. Biol.*, 7:4089-99 (1987).
Muzyczka, Use of Adeno-Associated Virus as a General Transduction Vector for Mammalian Cells, *Curr. Top. Microbiol. Immunol.*, 158:97-129 (1992).
Nakatani et al., Transgenic expression of a myostatin inhibitor derived from follistatin increases skeletal muscle mass and ameliorates dystrophic pathology in mdx mice. *FASEB J.*, 22:477-87 (2008).
Nathwani et al., Adenovirus-associated virus vector-mediated gene transfer in hemophilia B. *N. Engl. J. Med.*, 365:2357-65 (2011).
Neri et al., Dystrophin levels as low as 30% are sufficient to avoid muscular dystrophy in the human. *Neuromuscul. Disord.*, 17:913-8 (2007).
Nigro et al., 42nd ENMC Sponsored International Workshop: X-linked cardiomyopathies, Jun. 21-23, 1996, Naarden, The Netherlands. *Neuromuscul Disord* 7:397-403 (1997).
Ohnishi et al., Activin A is an autocrine activator of rat pancreatic stellate cells: potential therapeutic role of follistatin for pancreatic fibrosis. *Gut.*, 52:1487-93 (2003).

Patella et al., Follistatin attenuates early liver fibrosis: effects on hepatic stellate cell activation and hepatocyte apoptosis. *Am. J. Physiol. Gastrointest. Liver Physiol.*, 290:G137-44 (2006).
Paul et al., Increased viral titer through concentration of viral harvests from retroviral packaging lines, *Human Gene Therapy*, 4:609-15 (1993).
Perrin et al., An experimental rabies vaccine produced with a new BHK-21 suspension cell culture process: use of serum-free medium and perfusion-reactor system. *Vaccine*, 13:1244-50 (1995).
Pontera et al., 2q31.2q32.3 deletion syndrome: report of an adult subject. *Am. J. Med. Genet.* 149A:706-12 (2009).
Rodino-Klapac et al., Micro-dystrophin and follistatin co-delivery restores muscle function in aged DMD model. *Hum. Mol. Genet.*, 22:4929-37 (2013).
Romero et al., Phase I study of dystrophin plasmid-based gene therapy in Duchenne/Becker muscular dystrophy. *Hum. Gene. Ther.*, 15:1065-76 (2004).
Rosales et al., Impaired regeneration in LGMD 2A supported by increased Pax7 positive satellite cell content and muscle specific microRNA dysregulation. *Muscle Nerve*, 47:731-9 (2013).
Ruffing et al., Mutations in the carboxy terminus of adeno-associated virus 2 capsid proteins affect viral infectivity: lack of an RGD integrin-binding motif. *J Gen Virol*, 75: 3385-92 (1994).
Samulski et al., Cloning of adeno-associated virus into pBR322: rescue of intact virus from the recombinant plasmid in human cells. *Proc. Natl. Acad. Sci. USA*, 79:2077-81 (1982).
Samulski et al., Helper-free stocks of recombinant adeno-associated viruses: normal integration does not require viral gene expression. *J. Virol.*, 63:3822-8 (1989).
Schenpp et al., Highly purified recombinant adeno-associated virus vectors. Preparation and quantitation. *Methods Mol. Med.*, 69:427-43 (2002).
Schuelke et al., Myostatin mutation associated with gross muscle hypertrophy in a child. *N. Eng. J. Med.*, 350: 2682-2688 (2004).
Semenza et al., Hypoxia-inducible nuclear factors bind to an enhancer element located 3' to the human erythropoietin gene. *Proc. Natl. Acad. Sci. USA*, 88:5680-4 (1991).
Senapathy et al., Molecular cloning of adeno-associated virus variant genomes and generation of infectious virus by recombination in mammalian cells. *J. Biol. Chem.*, 259:4661-6 (1984).
Srivastava et al., Nucleotide sequence and organization of the adeno-associated virus 2 genome. *J. Virol.*, 45:555-64 (1983).
Sugino et al., Molecular heterogeneity of follistatin, an activin-binding protein: Higher affinity of the carboxyl-terminal truncated forms for heparan sulfate proteoglycans on the ovarian granulosa cell. *J. Biol. Chem.*, 268:15579-87 (1993).
Sunohara et al., Quadriceps myopathy: forme fruste of Becker muscular dystrophy. *Ann. Neurol.*, 28:634-9 (1990).
Tawil et al., Facioscapulohumeral muscular dystrophy (FSHD): design of natural history study and results of baseline testing. FSH-DY Group. *Neurology*, 44:442-6 (1994).
Tobin et al., Myostatin, a negative regulator of muscle mass: implications for muscle degenerative diseases, *Curr. Opin. Pharma.*, 5:328-32 (2005).
Tratschin et al., Adeno-associated virus vector for high-frequency integration, expression, and rescue of genes in mammalian cells. *Mol. Cell. Biol.*, 5:3251 (1985).
Tratschin et al., A Human Parvovirus, Adeno-Associated Birus, as a Eucaryotic Vector: Transient Expression and Encapsidation of the Procaryotic Gene for Chloramphenicol Acetyltransferase, *Mol. Cell. Biol.*, 4:2072 (1984).
van den Bergen et al., Dystrophin levels and clinical severity in Becker muscular dystrophy subjects. *J. Neurol. Neurosurg. Psychiatry*, 85:747-53 (2014).
Viollet et al., Utility of Cystatin C to monitor renal function in Duchenne muscular dystrophy. *Muscle Nerve*, 40:438-42 (2009).
Von Mitzlaff et al., Quadriceps myopathy as dystrophin-associated myopathy. *Schweiz Med. Wochenschr.*, 123:1865-69 (1993).
Wagner et al., A Phase I/II trial of MYO-029 in Adult Subjects with Muscular Dystrophy. *Ann. Neurol.*, 63:561-71 (2008).
Wagner et al., Loss of myostatin attenuates severity of muscular dystrophy in mdx mice. *Ann. Neurol*, 52:832-6 (2002).

(56) References Cited

OTHER PUBLICATIONS

Wagner, Muscle regeneration through myostatin inhibition. *Curr. Opin. Rheumatol.*, 17:720-4 (2005).
Walter et al., Creatine monohydrate in muscular dystrophies: A double-blind placebo-controlled clinical study. *Neurology*, 54:1848-50 (2000).
Weintraub et al., The myoD gene family: nodal point during specification of the muscle cell lineage. *Science*, 251:761-6 (1991).
Whittemore et al., Inhibition of myostatin in adult mice increases skeletal muscle mass and strength, *Biochem Biophys Res Commun.*, 300:965-971 (2003).
Winbanks et al., miR-206 represses hypertrophy of myogenic cells but not muscle fibers via inhibition of HDAC4. *PLoS One*, 8:e73589 (2013).
Witting et al., Effect of sildenafil on skeletal and cardiac muscle in Becker muscular dystrophy. *Ann. Neurol.*, 76(4):550-7 (2014).
Wolfman et al., Activation of latent myostatin by the BMP-1/tolloid family of metalloproteinases, *Proc. Natl. Acad. Sci. US*, 100:15842-6 (2003).
Xiao et al., Efficient long-term gene transfer into muscle tissue of immunocompetent mice by adeno-associated virus vector. *J. Virol.*, 70:8098-108 (1996).
Yaden et al.,. Follistatin: a novel therapeutic for the improvement of muscle regeneration. *J. Pharmacol. Exp. Ther.*, 349:355-71 (2014).
Zhu et al., Follistatin improves skeletal muscle healing after injury and disease through an interaction with muscle regeneration, angiogenesis, and fibrosis. *Am. J. Pathol.*,179:915-30 (2011).
Zimmers et al., Induction of cachexia in mice by systemically administered myostatin. *Science*, 296(5572):1486-8 (2002).
International Search Report and Written Opinion of the International Search Authority, European Patent Office, PCT/US2015/055022, dated Apr. 20, 2016.
International Preliminary Report on Patentability, PCT/US2015/055022, dated Apr. 11, 2017.

\* cited by examiner

Hormonal Profile

| Type | Start | End | Description |
|---|---|---|---|
| Region | 1 | 138 | Inverted terminal repeat |
| REGION | 139 | 804 | CMV enhancer/promoter (CMV) |
| REGION | 805 | 1298 | β-globin intron |
| GENE | 1362 | 2396 | Human follistatin isoform 344 cDNA |
| REGION | 2403 | 2881 | Human growth hormone polyA signal |
| REGION | 2921 | 3050 | Inverted terminal repeat |
| GENE | 3828 | 4625 | Kanamycin resistance gene |
| REGION | 3153 | 3459 | Plasmid origin of replication (ori) |

SEQUENCE LISTING

```
<160> NUMBER OF SEQ ID NOS: 9

<210> SEQ ID NO 1
<211> LENGTH: 1035
<212> TYPE: DNA
<213> ORGANISM: Homo sapiens
```

<400> SEQUENCE: 1

```
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaatgccg aatgaacaag aagaacaaac ccgctgcgt ctgcgccccg      360
gattgttcca acatcacctg aagggtcca gtctgcgggc tggatgggaa aacctaccgc     420
aatgaatgtg cactcctaaa ggcaagatgt aaagagcagc agaactggaa gtccagtac     480
caaggcagat gtaaaaagac ttgtcgggat gttttctgtc caggcagctc acatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
agaaaggcta cctgcctgct gggcagatct attggattag cctatgaggg aaagtgtatc     720
aaagcaaagt cctgtgaaga tatccagtgc actggtggga aaaaatgttt atgggatttc     780
aaggttggga gaggccggtg ttccctctgt gatgagctgt gccctgacag taagtcggat     840
gagcctgtct gtgccagtga caatgccact tatgccagcg agtgtgccat gaaggaagct     900
gcctgctcct caggtgtgct actggaagta aagcactccg gatcttgcaa ctccatttcg     960
gaagacaccg aggaagagga ggaagatgaa gaccaggact acagctttcc tatatcttct    1020
attctagagt ggtaa                                                     1035
```

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2

```
tggaaatccc cgtgagtcaa                                                   20
```

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3

```
catggtgatg cggttttg                                                     18
```

<210> SEQ ID NO 4
<211> LENGTH: 22
<212> TYPE: DNA
<213> ORGANISM: Artificial Sequence
<220> FEATURE:
<223> OTHER INFORMATION: Synthetic probe

<400> SEQUENCE: 4

```
ccgctatcca cgcccattga tg                                                22
```

<210> SEQ ID NO 5
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 5
cgaacatcga ttgaattccc                                               20

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
cttgctcagt tcggtctt                                                 18

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tggaaatccc cgtgagtcaa                                               20

<210> SEQ ID NO 8
<211> LENGTH: 18
<212> TYPE: DNA
<213> ORGANISM: Artificial sequence
<220> FEATURE:
<223> OTHER INFORMATION: Synthetic primer

<400> SEQUENCE: 8
atggtgatgc ggttttgg                                                 18

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
ccgctatcca cgcccattga tg                                            22
```

GUIDED INJECTIONS FOR AAV GENE TRANSFER TO MUSCLE

This application claims priority to U.S. Provisional Patent Application No. 62/062,592 filed Oct. 10, 2014, which is incorporated by reference herein in its entirety.

FIELD

The disclosure relates to methods for treating subjects with musculoskeletal diseases or other muscle wasting by gene transfer with recombinant adeno-associated viruses (rAAV) encoding myostatin inhibitors such as follistatin-344. The rAAV are administered prior to development of diffuse muscle fibrosis in a subject, or the rAAV administration avoids regions of muscle fibrosis in a subject.

Incorporation by Reference of the Sequence Listing

This application contains, as a separate part of disclosure, a Sequence Listing in computer-readable form (filename: 45059PCT_SeqListing.txt; 3,251 bytes—ASCII text file created Oct. 9, 2015) which is incorporated by reference herein in its entirety.

Background

Molecular advances have provided greater understanding of skeletal muscle diseases, such as muscular dystrophy (MD), beginning with the discovery of the dystrophin gene and its gene product. There are nine types of MD, each a genetic degenerative disease primarily affecting voluntary muscles.

Becker muscular dystrophy (BMD) is a clinical variant of dystrophin deficiency of muscle caused by a DMD gene mutation. The clinical course of BMD is milder compared to Duchenne muscular dystrophy (DMD), but there is wide variability in phenotype. There may be a delay in motor development, however in most cases reported symptoms relate to participation in sports in early teenage years. Lost ambulation is a major milestone that occurs in the fourth or fifth decade, although wheelchair independence is often preserved until after age sixty[1]. Cardiomyopathy is often the cause of death in BMD related to severe left ventricular dilation with reduced ejection fraction, complicated by life-threatening arrhythmias[2]. The majority of BMD subjects have deletions of the DMD gene, estimated at a frequency of 80%[3]. Other BMD causing mutations include missense mutations[4], exon duplications[5], and even out-of-frame exon deletions or nonsense mutations that predict no significant dystrophin translation[6,7]. Attempts to define the clinical course by dystrophin on muscle biopsy have been disappointing[8,9].

For clinical trials, there is consensus that distinction of BMD from DMD relies not on the specific mutation or dystrophin protein levels on muscle biopsy, but rather on the ability to maintain ambulation beyond age 16 years[7,10,11]. Another key feature of the ambulatory BMD subject is the targeted weakness of the quadriceps muscles (knee extensors)[10,12,13]. This can be relatively selective, so much so that it manifests as a form fruste, referred to as quadriceps myopathy[14]. Often it is this selective lower extremity weakness that predisposes subjects to frequent falls and is a key determinate in maintaining independent ambulation. Increasing muscle strength in BMD is challenging and no treatment modality has been identified[15,16]. Of interest, the benefit of glucocorticoids as demonstrated for the dystrophinopathy in the DMD population has not proved effective in BMD[17].

Research has shown that skeletal muscle utilizes a regulatory mechanism to control tissue mass. In a screen for novel members of the transforming growth factor-β (TGF-β) superfamily of growth and differentiation factors, myostatin [previously called growth and differentiation factor-8 (GDF-8)] was identified and has subsequently been shown to be a negative regulator of muscle formation. Myostatin is expressed in the myotome compartment of developing somites at E9.5 with expression continuing throughout adulthood, predominantly in skeletal muscles and adipose tissue. Myostatin is synthesized in a precursor form that undergoes two proteolytic processing events to remove the N-terminal signal sequence and the C-terminal fragment, which possess receptor-binding activity. Following proteolytic processing, the propeptide and the disulfide linked C-terminal dimer remain bound noncovalently in a latent complex. Myostatin can be activated by dissociation of the propeptide after proteolytic cleavage by a metalloproteinase of the bone morphogenic (BMP)/tolloid family. The dissociated C-terminal fragment is thus the biologically active species. For a review of the biosynthesis and signaling pathway of myostatin, see Lee, *Ann Rev Cell Dev Biol*, 20: 61-86 (2004).

Myostatin is conserved among species, especially in its C-terminal fragment which is identical across human, rat, murine, porcine, turkey and chicken species. Mutations within myostatin have been shown to be linked to the double muscling phenotype in cattle [Grobet et al., *Nat Genet*, 17: 71-74 (1997); Kambadur et al., *Genome Res*, 7:910-915 (1997); and McPherron and Lee, *Proc Natl Acad Sci USA*, 94:12457-12461 (1997)] and gross muscle hypertrophy in human subjects [Schuelke et al., *N Eng J Med*, 350: 2682-2688 (2004)]. Forced muscle atrophy has even been achieved with recombinant myostatin administration or over-expression of myostatin [Zimmers et al., *Science*, 296 (5572): 1486-1488 (2002)]. Histology of muscles from myostatin null mice shows increased muscle mass resulting from hyperplasia and hypertrophy of the muscle with less fat and connective tissues.

The hypothesis that it may be beneficial to block, remove, or reduce myostatin to promote regeneration and reduce fibrosis in MD has been explored in animal studies. Wagner et al., *Ann Neurol*, 52: 832-836 (2002) describes data obtained from crossing myostatin null mutant mice with mdx mice (which are models for dystrophin deficiency) showing that mdx mice lacking myostatin were stronger and more muscular than their mdx counterparts. In addition, Bogdanovich et al., *Nature*, 420: 418-421 (2002) report that when a neutralizing antibody to myostatin was administered to 4 week old mdx mice by intraperitoneal injection, an increase in body weight, muscle mass, muscle size and absolute muscle strength along with a significant decrease in muscle degeneration and concentrations of serum creatine kinase was observed. Similarly, Whittemore et al., *Biochem Biophys Res Commun*, 300: 965-971 (2003) describes that myostatin neutralizing antibodies increase muscle mass in adult mice. Tobin and Celeste, *Curr Opin Pharma*, 5: 328-332 (2005) reviews the myostatin pathway as well as studies testing the effects of reducing myostatin expression/activity.

Another review article, Wagner, *Curr Opin Rheumatol*, 17: 720-724 (2005), lists various therapeutic approaches of inhibiting myostatin that have been considered for treating human disease. For example, Wyeth has developed a humanized, anti-myostatin antibody called MYO-029 for clinical trials for treatment of muscular dystrophy in adult subjects. The review article states the antibody or similar agent will hopefully be tested in other indications such as inflammatory myopathies, cachexia and sarcopenia. The author also notes that a number of endogenous inhibitors of myostatin, including the myostatin propeptide, follistatin, FLRG and GASP-1 could be modified for use as therapeutic agents. The review refers to two articles describing the effects of modified propeptide on muscle in mice, Wolfman et al., *Proc Natl Acad Sci US*, 100: 15842-15846 (2003) and Bogdanovich et al., *FASEB J*, 19: 543-549 (2004).

The Wagner review article states that there is significant data that follistatin is an in vivo inhibitor of myostatin and refers to the results of studies described in Lee and McPherron, *Proc Natl Acad Sci USA*, 98(16): 9306-9311 (2001) and Amthor et al., *Developmental Biol.*, 270: 19-30 (2004) to support that statement. Follistatin is a secreted protein that inhibits the activity of TGF-β family members such as GDF-11/BMP-11. Follistatin-344 is a follistatin precursor that undergoes peptide cleavage to form the circulating Follistatin-315 isoform which includes a C-terminal acidic region. It circulates with myostatin propeptide in a complex that includes two other proteins, follistatin related gene (FLRG) and GDF associated serum protein (GASP-1). Follistatin-317 is another follistatin precursor that undergoes peptide cleavage to form the membrane-bound Follistatin-288 isoform. The Follistatin-288 isoform, which lacks a C-terminal acidic region, exhibits strong affinity for heparin-sulfate-proteoglycans, is a potent suppressor of pituitary follicle stimulating hormone, is found in the follicular fluid of the ovary, and demonstrates high affinity for the granulose cells of the ovary. The testes also produce Follistatin-288. Lack of follistatin results in reduced muscle mass at birth.

In the experiments described in the Lee and McPherron article, follistatin was over-expressed in transgenic mice. The mice showed increased muscling resulting from a combination of hyperplasia (increased muscle fiber number) and hypertrophy (increased muscle fiber diameter). The article proposes that follistatin binds the C-terminal dimer of myostatin and, in turn, inhibits the ability of myostatin to bind to activin type II receptors. Transgenic mice expressing high levels of myostatin propepetide or a dominant-negative form of activin type II receptor (Act RIIB) were also shown to exhibit increased muscle mass in the article.

The Amthor et al. article is stated to report that follistatin directly binds myostatin with high affinity, is co-expressed with myostatin in somites and prevents myostatin-mediated inhibition of limb muscle development in chick embryos. Indicating that the inhibitory effects of follistatin are not specific to myostatin evening in regard to muscle growth, the Wagner review article alternatively indicates that FLRG and GASP-1, which bind to and inhibit circulating myostatin, may prove to be specific inhibitors of myostatin for therapeutic use. FLRG is a protein that exhibits homology to a 10-cysteine repeat in follistatin. Hill et al., *J Biol Chem*, 277(43): 40735-40741 (2002) reports that FLRG binds circulating myostatin in vivo.

Yet another review article addressing the regulation of muscle mass by myostatin and clinical implications is Lee, *Annu Rev Cell Dev Biol.*, 20: 61-86 (2404).

See also, Kaspar and Mendell, WO 2008/067480.

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther*, 8: 659-669 (1997); Kessler et al., *Proc Nat. Acad Sc. USA*, 93: 14082-14087 (1996); and Xiao et al., *J Virol*, 70: 8098-8108 (1996). See also, Chao et al., *Mol Ther*, 2:619-623 (2000) and Chao et al., *Mol Ther*, 4:217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA*, 94: 5804-5809 (1997) and Murphy et al., *Proc Natl Acad Sci USA*, 94: 13921-13926 (1997). Moreover, Lewis et al., *J Virol*, 76: 8769-8775 (2002) demonstrated that skeletal myofibers possess the necessary cellular factors for correct antibody glycosylation, folding, and secretion, indicating that muscle is capable of stable expression of secreted protein therapeutics.

BRIEF SUMMARY

In one aspect, the disclosure provides methods of enhancing muscle function in a subject with a musculoskeletal disease or with muscle wasting not associated with a musculoskeletal disease comprising the step of administering to the subject by one or more intramuscular injections a composition comprising infectious encapsidated rAAVs, each rAAV comprising a rAAV genome comprising AAV inverted terminal repeats flanking a polynucleotide encoding follistatin-344, wherein the polynucleotide is operatively linked to transcriptional control DNA and wherein the genome lacks AAV rep and cap DNA, wherein the administration is prior to development of diffuse muscle fibrosis in the subject or wherein the intramuscular injection or injections avoid regions of muscle fibrosis in the subject. In some embodiments, the injections are guided by magnetic resonance imaging or positron emission tomography.

In some embodiments of the methods, the musculoskeletal disease is Becker muscular dystrophy. In some embodiments in which the musculoskeletal disease is Becker muscular dystrophy, the rAAV is injected bilaterally in the quadriceps and the dose injected is at least about $6\times10^{11}$ vg/kg/leg or at least about 1.2e12 vg/kg/subject.

In some embodiments of the methods, the musculoskeletal disease is Duchenne muscular dystrophy. In some embodiments in which, the musculoskeletal disease is Duchenne muscular dystrophy the rAAV is injected bilaterally in the quadriceps and the dose injected is at least about $2\times10^{11}$ vg/kg/leg or at least about 6e11 vg/kg/subject.

In some embodiments of the methods, the musculoskeletal disease is inclusion body myositis (familial or sporadic). In some embodiments of the methods in which the musculoskeletal disease is inclusion body myositis (familial or sporadic), the rAAV is injected bilaterally in the quadricep, gluteal and tibialis anteriaor muscles and the dose injected is at least about 1.2e12 vg/kg/limb.

Muscle fibrosis involves the replacement of muscle with connective tissue. Regions of muscle fibrosis can be identified by methods known in the art, for example, by magnetic resonance imaging (MRI). Patchy muscle fibrosis develops before diffuse muscle fibrosis during disease progression.

In another aspect, the disclosure provides methods of enhancing muscle function in a subject with Becker muscular dystrophy comprising the step of administering to the subject by one or more intramuscular injections a composition comprising infectious encapsidated rAAVs, each rAAV comprising a rAAV genome comprising AAV inverted terminal repeats flanking a polynucleotide encoding follistatin-344, wherein the polynucleotide is operatively linked to transcriptional control DNA and wherein the genome lacks AAV rep and cap DNA, wherein the rAAV dose injected is at least about $6\times10^{11}$ vg/kg/leg or 1.2e12 vg/kg/subject. In some embodiments, the rAAV is injected bilaterally in the quadriceps.

In yet another aspect, the disclosure provides methods of enhancing muscle function in a subject with Duchenne muscular dystrophy comprising the step of administering to the subject by one or more intramuscular injections a composition comprising infectious encapsidated rAAVs, each rAAV comprising a rAAV genome comprising AAV inverted terminal repeats flanking a polynucleotide encoding follistatin-344, wherein the polynucleotide is operatively linked to transcriptional control DNA and wherein the genome lacks AAV rep and cap DNA, wherein the rAAV dose injected is at least about $2\times10^{11}$ vg/kg/leg or at least about 6e11 vg/kg/subject. In some embodiments, the rAAV is injected bilaterally in the quadriceps.

In still another aspect, the disclosure provides methods of enhancing muscle function in a subject with inclusion body myositis (familial or sporadic) comprising the step of administering to the subject by one or more intramuscular injections a composition comprising infectious encapsidated rAAVs, each rAAV comprising a rAAV genome comprising AAV inverted terminal repeats flanking a polynucleotide encoding follistatin-344, wherein the polynucleotide is operatively linked to transcriptional control DNA and wherein the genome lacks AAV rep and cap DNA, wherein the rAAV dose injected is at least about 1.2e12 vg/kg/limb. In some embodiments, the rAAV is injected bilaterally in the quadriceps, gluteal and anterial tibialis muscles.

In some embodiments of all the foregoing methods, the infectious encapsidated rAAV administered is AAV1.CMV.FS344.

Methods described herein result in muscle enhancement, muscle function enhancement and/or increased muscle health in subjects.

DETAILED DESCRIPTION

Figure 1:
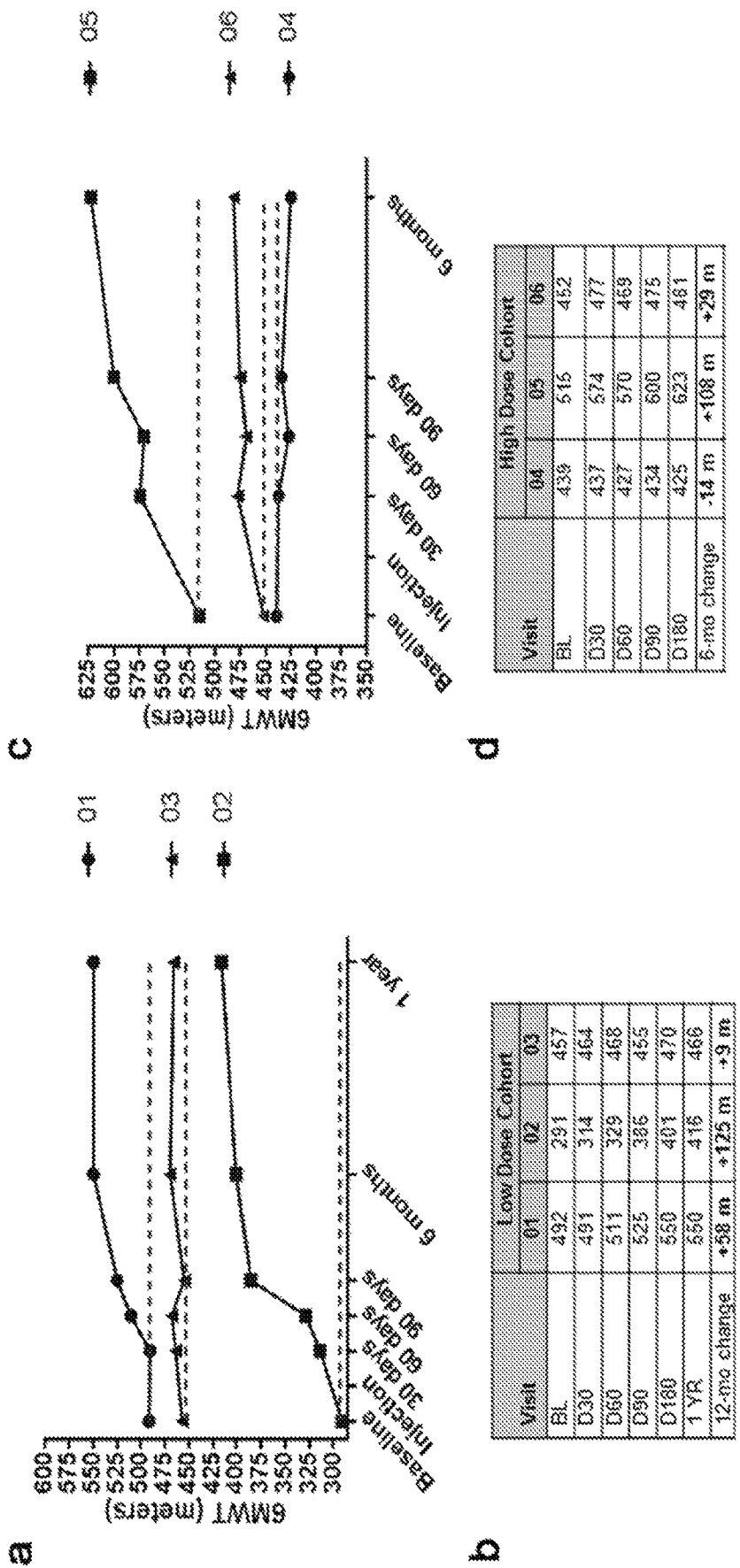
FIG. 1. Distance walked in six minute walk test (6MWT) following follistatin gene therapy. (a) Distance walked in meters in the 6MWT for subjects receiving AAV1.CMV.FS344 in each leg ($3\times10^{11}$ vg/kg/leg) with follow up for 1 year. A stippled red line shows the baseline for each subject. Subjects are numbered consecutively based on treatment at approximately 4-6 week intervals. (b) The table shows the exact distances at each time point from baseline (BL) to 1 year. The "12-mo change" indicates the distance walked compared to BL. D=day. (c) Distance walked in meters in the 6MWT for subjects receiving AAV1.CMV.FS344 in each leg ($6\times10^{11}$ vg/kg/leg) with follow up for 6 months. (d) The table again shows the exact distances at each time point from baseline (BL) to 6 months. The "6-mo change" indicates the distance walked compared to BL. D=day FIG. 2. Interferon-gamma (INF-γ) ELISpot assays. The T cell immune responses to AAV1 capsid and follistatin are shown for each subject throughout the clinical trial. Spot forming cells (SFCs) per million peripheral blood mononuclear cells (PBMCs) are shown on the Y-axis, and days post infection (dpi) on X-axis.

The present disclosure provides methods and materials useful for gene therapy for enhancing muscle, enhancing muscle function, and/or enhancing muscle health in a subject with a musculoskeletal disease [for example, BMD, DMD and inclusion-body myositis (IBM; familial or sporadic)] or in a subject with muscle wasting not associated with a musculoskeletal disease. The methods of the disclosure involve delivering inhibitors of myostatin, a regulator of muscle mass, to muscle cells in the subject. Subjects include, but are not limited to, mammals. In some embodiments, the subjects are human subjects. In some embodiments, the subjects are human pediatric subjects. In some embodiments, the subject has a muscular dystrophy. In some embodiments, the subject has BMD. In some embodiments, the subject has DMD. In some embodiments, the subject has IBM.

The terms "muscle enhancement" and "enhancing muscle" are intended to be interchangeable herein and include, but are not limited to, inducement of hyperplasia (increased muscle fiber number), inducement of hypertrophy (increased muscle fiber diameter) or both. "Enhanced muscle function" or "enhancing muscle function" are intended to be interchangeable herein and include, but are not limited to, one or more of decreased atrophy, increased muscle endurance, increased muscle force and increased muscle strength. "Increased muscle health" includes, but is not limited to reduced muscle fibrosis, reduced muscle inflammation, or both. "Muscle wasting" is also known as muscle atrophy. Muscle wasting can be associated with a musculoskeletal disease, but it can also occur in subjects that don't have a musculoskeletal disease.

Some embodiments of the disclosure exploit the unique properties of AAV to deliver polynucleotides encoding myostatin inhibitors such as follistatin-344 to muscle cells.

In various methods contemplated herein, subjects are pre-assessed for muscle fibrosis and if muscle fibrosis is found the delivery of rAAV to a subject avoids areas of muscle fibrosis. In some embodiments, the subjects are assessed and rAAV delivery is guided by MRI or by positron emission tomography (PET). MRI is used to visualize muscle cells in the art. See, for example, Mercuri et al., *Eur. J. Paediatric Neurology*, 6: 305-307 (2002); Mercuri et al., *Eur. J. Paediatric Neurology*, 6: 309-314 (2002); and Kinali et al., *Lancet Neurol.*, 8: 918-928 (2009).

In an aspect, the disclosure provides rAAV genomes. The rAAV genomes comprise one or more AAV ITRs flanking a polynucleotide encoding one or more myostatin inhibitors. If the polynucleotide encodes one or more myostatin inhibitor proteins the polynucleotide is operatively linked to transcriptional control DNA, specifically promoter DNA and polyadenylation signal sequence DNA that are functional in target cells to form a gene cassette. The gene cassette may also include intron sequences to facilitate processing of the RNA transcript when expressed in mammalian cells. Alternatively, the polynucleotide in the rAAV genome be a myostatin inhibitor RNA or may encode one or more myostatin inhibitor RNAs. The myostatin inhibitor RNAs may be antisense RNAS, ribozymes, small interfering RNAs (RNAi) or aptamers that inhibit expression of myostatin or its receptor activin IIb. For example, an antisense RNA complementary to the translation initiation site of myostatin or activin IIb may be encoded by the rAAV genome. As another example, an RNA that binds to the myostatin or activin IIb double-stranded DNA may be encoded that prevents DNA unwinding and transcription. As yet another example, commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom siRNA molecules. In addition, commercially kits are available to produce custom siRNA molecules, such as SILENCER™ siRNA Construction Kit (Ambion Inc., Austin, Tex.) or psiRNA System (InvivoGen, San Diego, Calif.).

The rAAV genomes of the disclosure lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11.The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC 001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Other AAV serotypes are known in the art.

In another aspect, the disclosure provides DNA plasmids comprising rAAV genomes of the disclosure. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The disclosure thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

In another aspect, the disclosure provides rAAV (i.e., infectious encapsidated rAAV particles) comprising a rAAV genome of the disclosure. Embodiments include, but are not limited to, the exemplified rAAV referred to herein as "AAV1.FS344" or "rAAV1.CMV.FS344." The rAAV.CMV.FS344 genome includes in sequence an AAV2 ITR, the CMV promoter, an intron from the human β-globin gene, the follistatin-344 DNA, the human growth hormone polyadenylation termination signal and another AAV2 ITR. The follistatin-344 DNA (5' to 3') is SEQ ID NO: 1
```
atggtccgcg cgaggcacca gccgggtggg ctttgcctcc tgctgctgct gctctgccag    60
ttcatggagg accgcagtgc ccaggctggg aactgctggc tccgtcaagc gaagaacggc    120
```

-continued

```
cgctgccagg tcctgtacaa gaccgaactg agcaaggagg agtgctgcag caccggccgg   180
ctgagcacct cgtggaccga ggaggacgtg aatgacaaca cactcttcaa gtggatgatt   240
ttcaacgggg gcgcccccaa ctgcatcccc tgtaaagaaa cgtgtgagaa cgtggactgt   300
ggacctggga aaaaatgccg aatgaacaag aagaacaaac cccgctgcgt ctgcgccccg   360
gattgttcca acatcacctg gaagggtcca gtctgcgggc tggatgggaa aacctaccgc   420
aatgaatgtg cactcctaaa ggcaagatgt aaagagcagc cagaactgga agtccagtac   480
caaggcagat gtaaaaagac ttgtcgggat gttttctgtc caggcagctc cacatgtgtg   540
gtggaccaga ccaataatgc ctactgtgtg acctgtaatc ggatttgccc agagcctgct   600
tcctctgagc aatatctctg tgggaatgat ggagtcacct actccagtgc ctgccacctg   660
agaaaggcta cctgcctgct gggcagatct attggattag cctatgaggg aaagtgtatc   720
aaagcaaagt cctgtgaaga tatccagtgc actggtggga aaaaatgttt atgggatttc   780
aaggttggga gaggccggtg ttccctctgt gatgagctgt gccctgacag taagtcggat   840
gagcctgtct gtgccagtga caatgccact tatgccagcg agtgtgccat gaaggaagct   900
gcctgctcct caggtgtgct actggaagta aagcactccg gatcttgcaa ctccatttcg   960
gaagacaccg aggaagagga ggaagatgaa gaccaggact acagctttcc tatatcttct  1020
attctagagt ggtaa                                                   1035
```

The genome lacks AAV rep and cap DNA, that is, there is no AAV rep or cap DNA between the ITRs of the genome.

In some embodiments, the FS-344 polynucleotide in a rAAV genome is the FS-344 DNA set out in the foregoing paragraph. In some embodiments, the is a variant polynucleotide having about 80%, 81%, 82%, 83%, 84%, 85%, 86%, 87%, 88%, 89%, 90%, 91%, 92%, 93%, 94%, 95%, 96%, 97%, 98% or 99% sequence identity to the FS-344 DNA above. In some embodiments, the variant FS-344 polynucleotide encodes the same FS-344 polypeptide as the polypeptide encoded by the FS-344 DNA set out above. In some embodiments, the variant FS-344 polynucleotide encodes a variant FS-344 polypeptide with at least one amino acid sequence alteration as compared to the amino acid sequence of the polypeptide encoded by the FS-344 DNA set out above. An amino acid sequence alteration can be, for example, a substitution, a deletion, or an insertion of one or more amino acids, preferably conservative substitutions. A variant FS-344 polypeptide can have any combination of amino acid substitutions, deletions or insertions as long as the activity of the polypeptide is retained. In one aspect, a variant FS-344 polypeptide can have a number of amino acid alterations such that its amino acid sequence shares at least 60, 70, 80, 85, 90, 95, 97, 98, 99 or 99.5% identity with the amino acid sequence encoded by the FS-344 cDNA above.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69 427-443 (2002); U.S. Pat. No. 6,566,118 and WO 98/09657.

In another embodiment, the invention contemplates compositions comprising rAAV of the present disclosure. These compositions may be used to enhance muscle and/or improve muscle function. In one embodiment, compositions of the disclosure comprise a rAAV encoding a myostatin inhibitor of interest. In other embodiments, compositions of the present disclosure may include two or more rAAV encoding different myostatin inhibitors of interest.

Compositions of the disclosure comprise rAAV in a pharmaceutically acceptable carrier. The compositions may also comprise other ingredients such as diluents and adjuvants. Acceptable carriers, diluents and adjuvants are non-toxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG). In some embodiments, the rAAV is formulated in 20 mM Tris (pH 8.0), 1 mM $MgCl_2$ and 200 mM NaCl containing 0.001% pluronic F68.

Titers of rAAV to be administered in methods of the disclosure will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). Methods for titering AAV are described in Clark et al., *Hum. Gene Ther.*, 10: 1031-1039 (1999). In some embodiments, the dose administered to a subject is about $3\times10^{11}$ vg/kg/leg to about $6\times10^{11}$ vg/kg/leg (e.g., divided into four injections administered over the three major muscle groups of the quadriceps) or more, or about 6e11 vg/kg/subject to about 1.2e12 vg/kg/subject or more. In some embodiments, the dose administered to a subject is at least about $3\times10^{11}$ vg/kg/leg (e.g., divided into four injections administered over the three major muscle groups of the quadriceps) or 6e11 vg/kg/subject. In some embodiments, the dose administered to a subject is at least about $6\times10^{11}$ vg/kg/leg (e.g., divided into four injections administered over the three major muscle groups of the quadriceps) or 1.2e12 vg/kg/subject. In some embodiments, the dose is 2e11 vg/kg/quad, 6e11 vg/kg/quad (divided among 12 injection sites) or 6e11 vg/kg/quad (divided among 14 injection sites). In some embodiments, the dose is 1e12 vg/kg/limb (divided among 18 injection sites in quadricepts, gluteal and tibialis anterior muscles in each limb).

Methods of transducing a target cell with rAAV, in vivo or in vitro, are contemplated by the disclosure. The in vivo methods comprise the step of administering an effective dose, or effective multiple doses, of a composition comprising a rAAV of the disclosure to a subject (including a human subject) in need thereof. If the dose is administered prior to development of a disorder/disease, the administration is prophylactic. If the dose is administered after the development of a disorder/disease, the administration is therapeutic. In some embodiments of the disclosure, an effective dose is a dose that alleviates (eliminates or reduces) at least one symptom associated with the disorder/disease state being treated (e.g., BMD, DMD or IBM), that slows or prevents progression to a disorder/disease state, that slows or prevents progression of a disorder/disease state, that diminishes the extent of disease, that results in remission (partial or total) of disease, and/or that prolongs survival. In some embodiments, an effective dose, or effective multiple doses, of a composition comprising a rAAV of the disclosure to a subject is a dose that prevents, slows progression of, or ameliorates (eliminates or reduces) muscle pathology associated musculoskeletal disorder being treated. An effect on muscle pathology can be demonstrated by an improvement in one or more measures standard in the art such as: absolute muscle specific force; force decrement during eccentric muscle contractions; serum CK level; serum cardiac troponin level; serum MMP9 level; grip strength; limb torque; limb mobility or flexibility; ambulation; 6-minute walk test (6MWT); knee flexor or extensor strength; maximal voluntary isometric muscle contraction; North Star Ambulatory Assessment; muscle mass, fat reduction, or edema by limb T2-weighted MRI measures; muscle contractures; limb joint angle; heart function (heart rate, cardiac output, percent fractional shortening, stroke volume); respiration (including respiratory rate, blood oxygenation, need for supplemental oxygen); muscle necrosis; muscle regeneration; muscle wasting; muscle inflammation; muscle calcification; muscle central nucleation; muscle size or myofiber size; lifespan; and dystrophin or laminin alpha 2 surrogate protein expression (utrophin, plectin 1, laminin alpha 5, agrin). See, for example, Forbes et al., *Radiology,* 269(1): 198-207 (2013); Govoni et al., *Cell Mol. Life Sci.,* 70(23): 4585-4602 (2013); and Chandrasekharan and Martin, *Methods Enzymol.,* 479: 291-322 (2010).

Combination therapies are also contemplated by the invention. Combination as used herein includes both simultaneous treatment or sequential treatments. Combinations of methods of the disclosure with standard medical treatments (e.g., corticosteroids for muscular dystrophies) are specifically contemplated, as are combinations with novel therapies. For example, for treatment of muscular dystrophies, methods of the disclosure may be combined with follistatin administration, followed by simultaneous or concomitant treatment to correct the genetic disorder. Correcting a genetic disorder may involve, for example, correcting or replacing dystrophin in disorders such as BMD, DMD or IBM. Given that in disorder contemplated for treatment by the present disclosure, significant amount of muscle is lost, the prevention or rescue of muscle will give a substrate (preserved or regenerated muscle) for subsequent gene correction. In this respect, it may be conceivable to inhibit myostatin to enhance muscle, increase muscle size, and then provide the secondary treatment. Such secondary treatments for Muscular Dystrophy may be IGF-1, interfering RNA approaches, exon-skipping, calpain inhibition, dystrophin upregulation, and dystroglycan expression. Further, there may be additions to myostatin inhibition approaches to enhance the muscle boosting effects. For example, addition of IGF-1 or other trophic factors or muscle precursor injections could be performed. Myostatin inhibition in concert with muscle precursor cells (satellite cells, stem cells) may allow more of these cells to be incorporated into the tissue.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of rAAV (in particular, the AAV ITRs and capsid protein) of the disclosure may be chosen and/or matched by those skilled in the art taking into account the infection and/or disease state being treated and the target cells/tissue(s) that are to express the myostatin inhibitor protein(s). In some embodiments, the route is one or more intramuscular injections into the quadriceps of the subject. In some embodiments, the route is one or more intramuscular injections into each of the three major muscle groups of the quadriceps of the subject.

In particular, actual administration of rAAV of the present disclosure may be accomplished by using any physical method that will transport the rAAV recombinant vector into the target tissue of an animal. Administration according to the disclosure includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the disclosure results in sustained expression of myostatin inhibitors. The present disclosure thus provides methods of administering/delivering rAAV which express myostatin inhibitors to an animal, preferably a human being. These methods include transducing tissues (including, but not limited to, tissues such as muscle, organs such as liver and brain, and glands such as salivary glands) with one or more rAAV of the present disclosure. Transduction may be carried out with gene cassettes comprising tissue specific control elements. For example, one embodiment of the disclosure provides methods of transducing muscle cells and muscle tissues directed by muscle specific control elements, including, but not limited to, those derived from the actin and myosin gene families, such as from the myoD gene family [See Weintraub et al., *Science*, 251: 761-766 (1990], the myocyte-specific enhancer binding factor MEF-2 [Cserjesi and Olson, *Mol Cell Biol* 11: 4854-4862 (1990], control elements derived from the human skeletal actin gene [Muscat et al., *Mol Cell Biol*, 7: 4089-4099 (1987)], the cardiac actin gene, muscle creatine kinase sequence elements [See Johnson et al., *Mol Cell Biol*, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypozia-inducible nuclear factors [Semenza et al., *Proc Natl Acad Sci USA*, 88: 5680-5684 (1991)], steroid-inducible elements and promoters including the glucocorticoid response element (GRE) [See Mader and White, *Proc. Natl. Acad. Sci. USA* 90: 5603-5607 (1993)], and other control elements.

Muscle tissue is an attractive target for in vivo gene delivery and gene therapy, because it is not a vital organ and is easy to access. The disclosure contemplates sustained expression of biologically active myostatin inhibitor proteins from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts. Since muscle tissue is readily accessible to the circulatory system, a protein produced and secreted by muscle cells and tissue in vivo will logically enter the bloodstream for systemic delivery, thereby providing sustained, therapeutic levels of protein secretion from muscle.

The term "transduction" is used to refer to the administration/delivery of myostatin inhibitor DNA to a recipient cell either in vivo or in vitro, via a replication-deficient rAAV of the disclosure resulting in expression of a functional myostatin inhibitor by the recipient cell.

Thus, the disclosure provides methods of administering an effective dose (or doses, administered essentially simultaneously or doses given at intervals) of rAAV that encode, for example, follistatin-344 to a subject in need thereof.

EXAMPLES

Aspects and embodiments of the invention are illustrated by the following non-limiting examples.

Example 1

Introduction

In a clinical trial, a strategy to achieve a clinically meaningful effect on muscle health and strength was applied to BMD through inhibition of the myostatin pathway. Extensive studies in the mdx mouse[18] and in non-human primates[19] supported this approach, demonstrating significant increases in strength by delivery of follistatin (FS) using adeno-associated virus (AAV). FS has been shown to function as a potent myostatin antagonist with the additional benefit of controlling muscle mass through pathways independent of the myostatin signaling cascade[20]. There are two isoforms of follistatin generated by alternative splicing and initially translated to isoforms FS317 and FS344[21]. Post translational modification of each cleaves a 29 amino acid signal peptide giving rise to FS288 and FS315. FS288 functions collaboratively in reproductive physiology with activin and inhibins of the hypothalamic pituitary-gonadal axis[22]. FS315 more reliably targets skeletal muscle, has no known cardiotoxicity or other adverse effects and is ideal for gene delivery to muscle.

AAV1.CMV.FS344 delivered by direct intramuscular injection to quadriceps and tibialis anterior muscles of the mdx mouse increased muscle mass and strength throughout the lower extremities with a demonstrable remote effect on these same parameters in the upper limbs and increased muscle mass in the paraspinal muscles[18]. This we attributed to the muscle acting as a secretory site for follistatin with the circulating isoform reaching remote sites[23]. AAV1.CMV.FS344 was further tested in the non-human primate to explore a paradigm applicable to clinical trial. In the cynomolgus macaque we injected AAV1.FS344 directly into the quadriceps muscle resulting in an increase in size and strength of this muscle[19].

These pre-clinical studies in the absence of toxicity enabled a Phase I/IIa clinical trial in subjects with BMD (IND 14845).

Results

Subject Characteristics and Response to Treatment

Six male BMD subjects were treated according to a dose-ascending gene therapy regimen (Table 1).

TABLE 1

Characteristics of Becker Muscular Dystrophy Subjects enrolled in Trial

| Cohort | Subject ID | Age (yrs) | DMD mutation |
|---|---|---|---|
| Cohort 1 | 01 | 30 | del exon 48-49 |
| AAV1.CMV.FS344 | 02 | 35 | point mutation exon 8[a] |
| ($3 \times 10^{11}$ vg/kg per leg) | 03 | 37 | del exon 45-48 |
| Cohort 2 | 04 | 34 | del exon 45-48 |
| AAV1.CMV.FS344 | 05 | 24 | del exon 45-47 |
| ($6 \times 10^{11}$ vg/kg per leg) | | | |
| (Cohort 2 cont.) | 06 | 30 | del exon 13 |

Abbreviations:
AAV1, adeno-associated virus serotype 1;
CMV: cytomegalovirus;
FS344: follistatin isoform 344;
kg, kilogram;
vg, vector genome;
del: deletion
[a]Subexonic deletion (c.676_678delAAG, p.226delLys) in exon 8 of the DMD gene This was a single site study conducted at Nationwide Children's Hospital. Enrolled subjects were ambulatory with knee extensor muscle weakness greater than 2 standard deviations below age expectations[24]. Participants were not on any immunosuppressive therapy at the time of recruitment, but were placed on prednisone one month prior to AAV1.CMV.FS344 injections as a precaution against an immune response to AAV capsid, as previously found in human clinical trials[25-27]. Prednisone dosing remained the same for approximately one month post injection and was tapered off by day 60 post gene delivery. T cell responses towards AAV1 capsid and follistatin were assessed by IFN-γ ELISpot assay and were <50 spot forming cells/million PBMCs for each participant upon enrollment. Serum neutralizing antibody titers to AAV1 were assessed by ELISA and were below 1:50 at the start of the study and monitored according to a previously published clinical trial schedule[26,27]. Muscle biopsies were performed 30 days prior to administration of AAV1.CMV.FS344 as a baseline histopathological assessment of muscle with a follow up biopsy on the opposite extremity at day 180 post gene transfer. The extremity undergoing initial biopsy was chosen by a randomization table and taken from the proximal vastus lateralis, thus determining the post biopsy site in the opposite extremity targeting the same head of the quadriceps. Serum chemistry/hematology batteries were assessed at baseline, days 7, 14, 30, 60, 90, 180, and 1 year to evaluate for adverse effects due to gene transfer and included: complete blood count, liver function studies, kidney function (cystatin C)[28], amylase, creatine kinase, and serum hormones (FSH, LH, testosterone, estrogen).

Cohort 1 included three ambulatory subjects, ages 30, 35 and 37 (34±3.6), genetically diagnosed with in-frame DMD gene mutations. Subjects in this cohort received $3\times10^{11}$ vg/kg/leg (total 6e11 vg/kg/subject) delivered to three of the four muscle groups of the quadriceps: the vastus lateralis (VL), rectus femoris (RF), and vastus medialis (VM). Four injections were delivered per muscle, each with the guidance of ultrasonography and a MyoJect Luer™ Lock EMG needle. This first Cohort has now been followed for 1year post gene delivery (FIG. 1). In two subjects improvement on the 6MWT was robust: Subject 01 improved by 58 meters, and Subject 02 by 125 meters. Subject 03 improved modestly, with an increase of 9 meters, however we would not consider this outside the range of variability for the BMD population, based on previous clinical experience. Although, no comparative natural history data of the 6MWT in BMD subjects is available, substantial increases in 6MWT as observed in our subjects would not be predicted over the course of 1 year in untreated BMD subjects.

Figure 2:
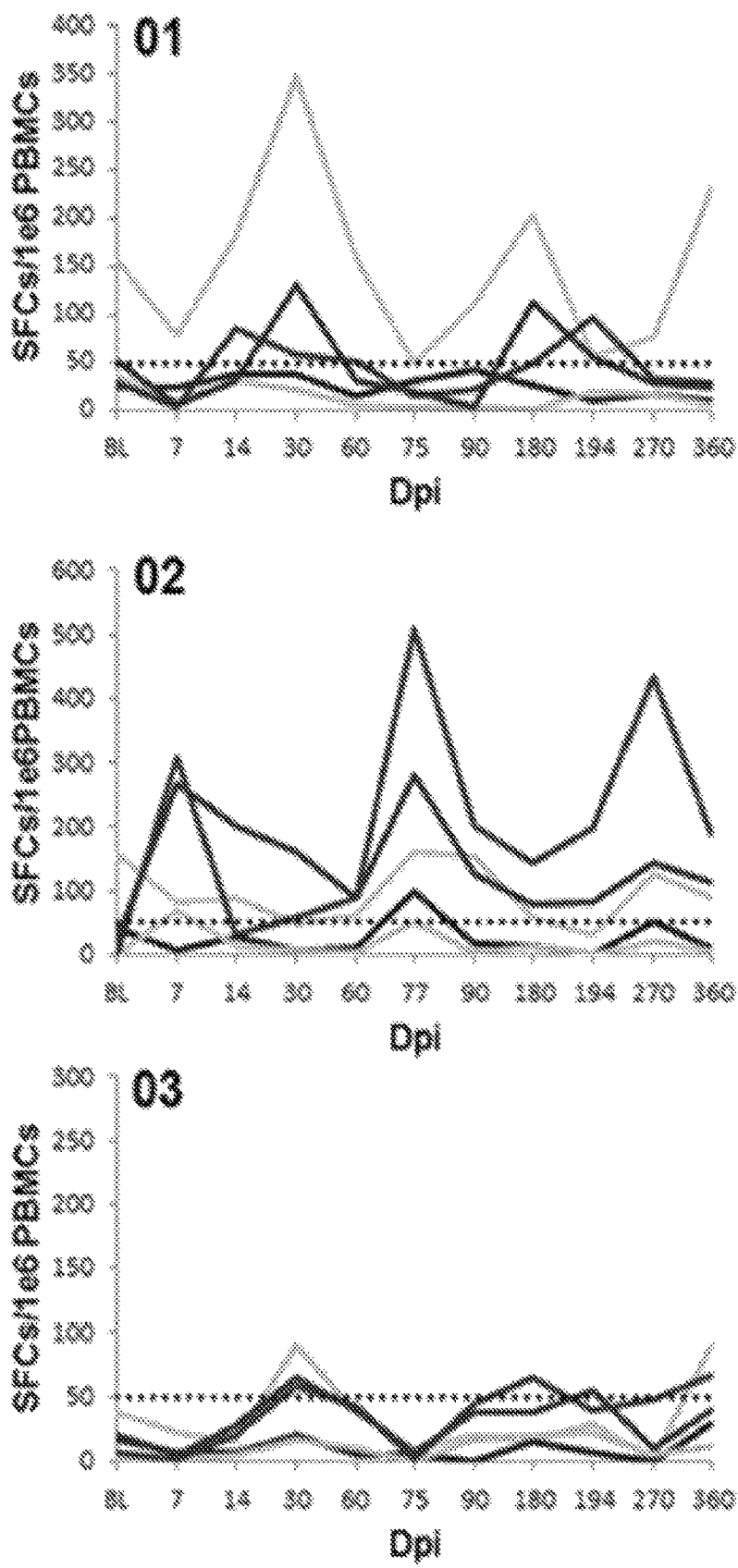
Figure 2:
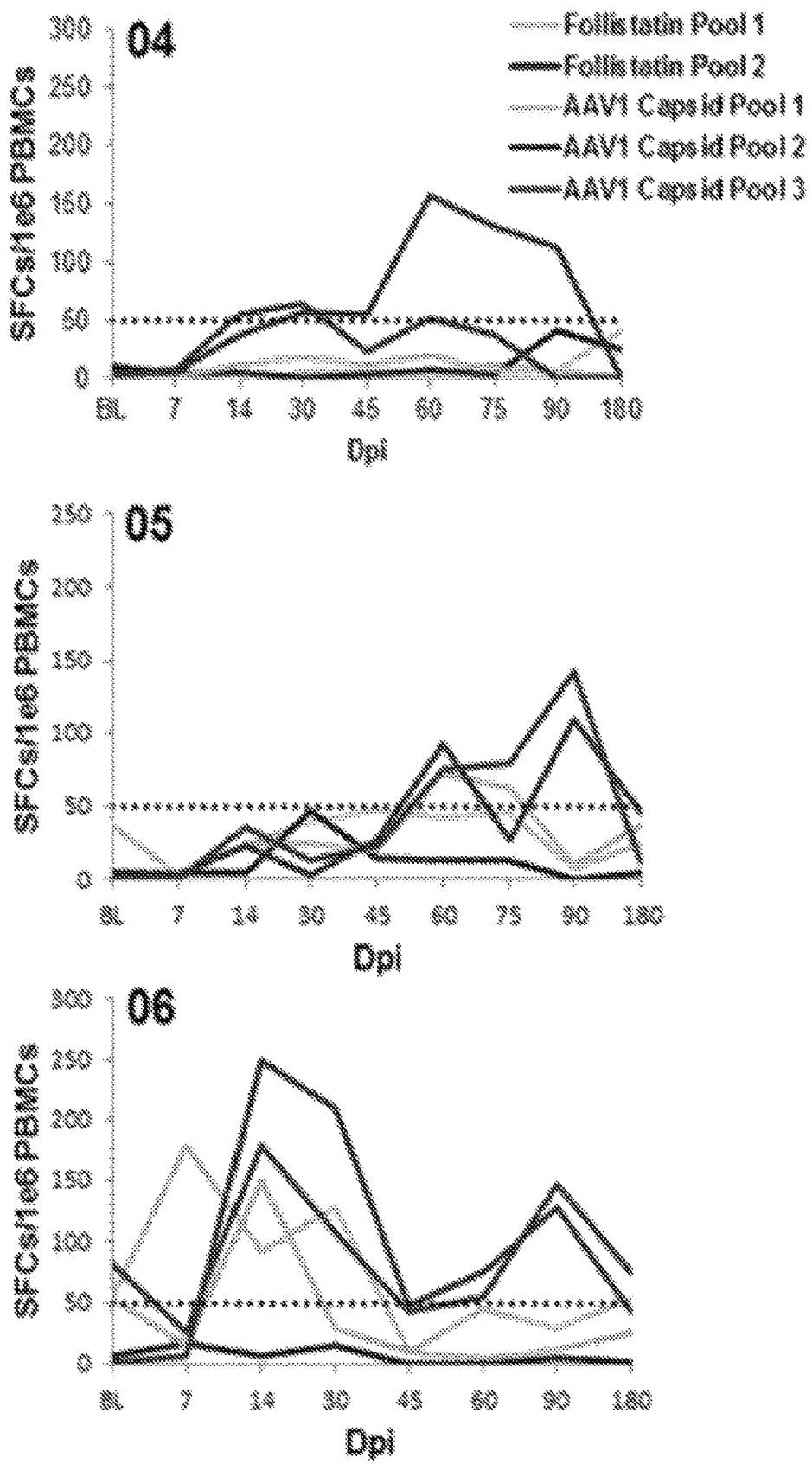

Furthermore, the improvement in walk distance in subjects 01 and 02 cannot be attributed to prednisone, since they had completely stopped the drug by day 90, while strength peaked at day 180 and was maintained throughout the remainder of the clinical trial. There were no significant adverse events during this trial that were related to gene transfer. No abnormalities were noted in any organ system assessment of liver, kidney, or bone marrow, and pituitary-gonadal hormone levels [FSH, LH, estrogen, testosterone (FIG. 8)] remained normal throughout the trial. Assessment of the IFN-γ ELISpot assay for T-cell immune responses to AAV1 capsid or follistatin showed no consistent or predictable response related to T cell immunity between subjects (FIG. 2). Of particular note, Subject 03 who achieved the least benefit in this cohort from gene transfer showed virtually no increase in T cell immunity throughout year 1, while Subject 02 showed an increase in T cells targeting AAV1, and subject 01 showed increased T cells to follistatin. Serum anti-follistatin antibody levels were never elevated above pretreatment levels (remained below 1:50 titer) in Cohort 1.

Based on the safety of Cohort 1, an additional three BMD subjects were enrolled in the ascending dose trial. Cohort 2 included ambulatory subjects ages 24, 30, and 34 (29±5.0) with in-frame DMD gene mutations (Table 1). The dose for this group was increased to $6\times10^{11}$ vg/kg/leg (1.2e12 vg/kg/subject). Gene delivery followed the paradigm described for the first cohort with delivery to the three major groups of the quadriceps: VL, RF, and VM. These three subjects (04, 05, 06) have now been followed for 6 months and the results of the 6MWT are shown in FIG. 1. It is likely that Cohort 2 subjects have received maximum benefit from gene transfer based on findings in the first cohort. Subject one of Cohort 2 (Subject 04) showed the least benefit of any subject in the trial. There was a decrease in the 6MWT by 14 meters. The other two subjects in this cohort improved their walking distance. Subject 05 increased by 108 meters, and Subject 06 by 29 meters, with improvements found as early as 1 month post gene delivery and maintained over 6-months.

In neither cohort did we find a consistent increase in quadriceps muscle strength following AAV.FS344 gene transfer. This finding follows a pattern we encountered in our clinical trial of eteplirsen for exon skipping where we also showed functional benefit in the 6MWT without increasing quadriceps strength over a similar duration of study.[29] We believe that muscle fibrosis is a barrier to increasing quantitative measures of muscle strength in single muscle groups, accounting for the poor correlation. The success we report here is related to follistatin gene therapy targeting a composite group of muscles contributing to the results of 6MWT because of the remote effect of secretion following FS344 transduced muscle fibers. Remote effects of AAV1.CMV.FS344 were apparent in pre-clinical studies in both mice and non-human primates.[18,19] Another factor contributing to outcomes was predicted by McDonald et al suggesting that longer duration studies may be necessary to increase absolute values of strength by myometry.[30]

In Cohort 2 subjects as in the low dose subjects, no significant adverse events were encountered, serum chemistries and hormone levels (FIG. 8) remained normal, and there was there was no consistent pattern of T cell immunity specific to AAV capsid pool as evaluated by ELISpot assays (FIG. 2). Subject 06 showed early and significant elevation of immune response to follistatin that was not present prior to gene transfer. Serum anti-follistatin antibody levels in Cohort 2 remained below 1:50 titers.

Gross Examination and MRI Results

Figure 3:
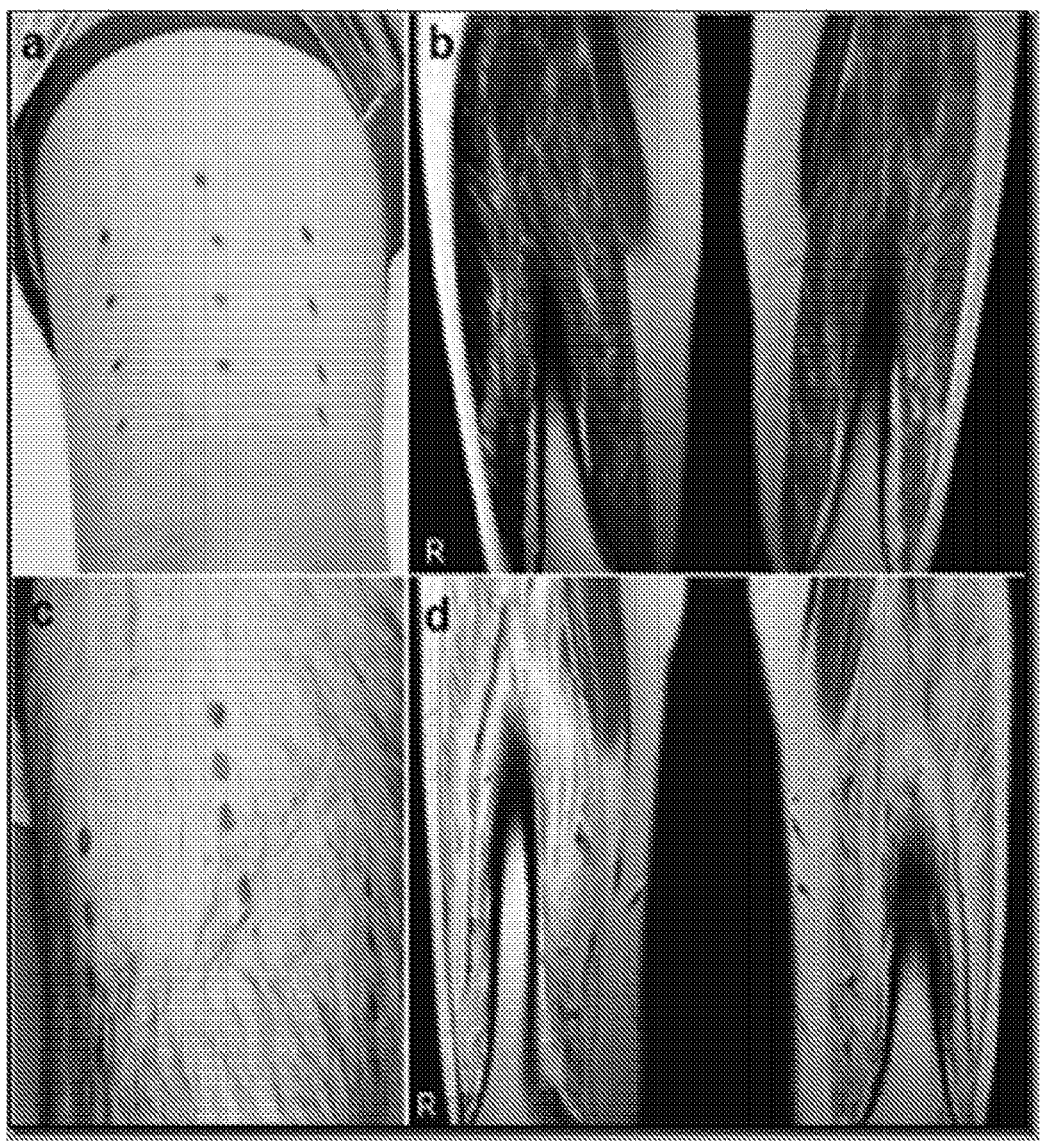
FIG. 3. Site of gene transfer on leg compared to areas of fibrosis. (a) The sites of gene transfer to the right leg is shown for Subject 05 (distance walked=108 m, 6MWT) using a surgical marking pen; (b) MRI of quadriceps muscles for Subject 05 shows a mild degree of MRI intensity (T1-weighted image); (c) the sites of gene transfer to the right leg is shown for Subject 03 (distance walked=9 6MWT) using a surgical marking pen; (d) MRI of quadriceps muscles for Subject 03 shows marked increase in intensity indicative of fibrosis.
Figure 4:
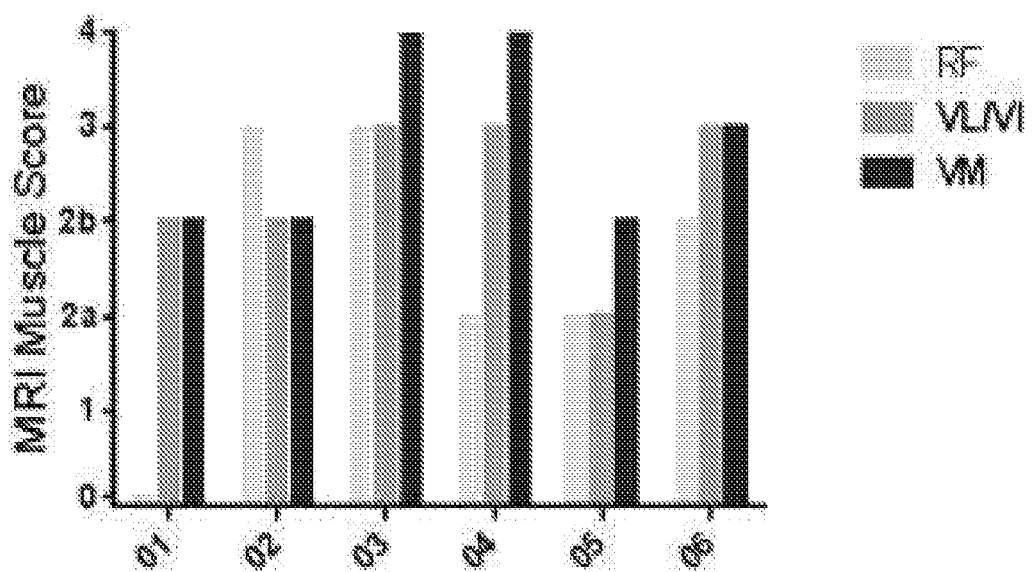
FIG. 4. Grading Scale for quadriceps muscles by Magnetic Resonance Images (MRI). Muscle MRIs were used to establish a grading scale for the quadriceps muscles based on approximate percentage of increased image intensity indicating degree of fibrosis replacing normal muscle. There was an overall correlation between fibrosis and distance walked on the 6MWT with Subjects 03 and 04 demonstrating the least benefit from gene transfer. RF=rectus femoris; VL/VI=vastus lateralis/vastus intermedius; VM=vastus medialis.
Figure 5:
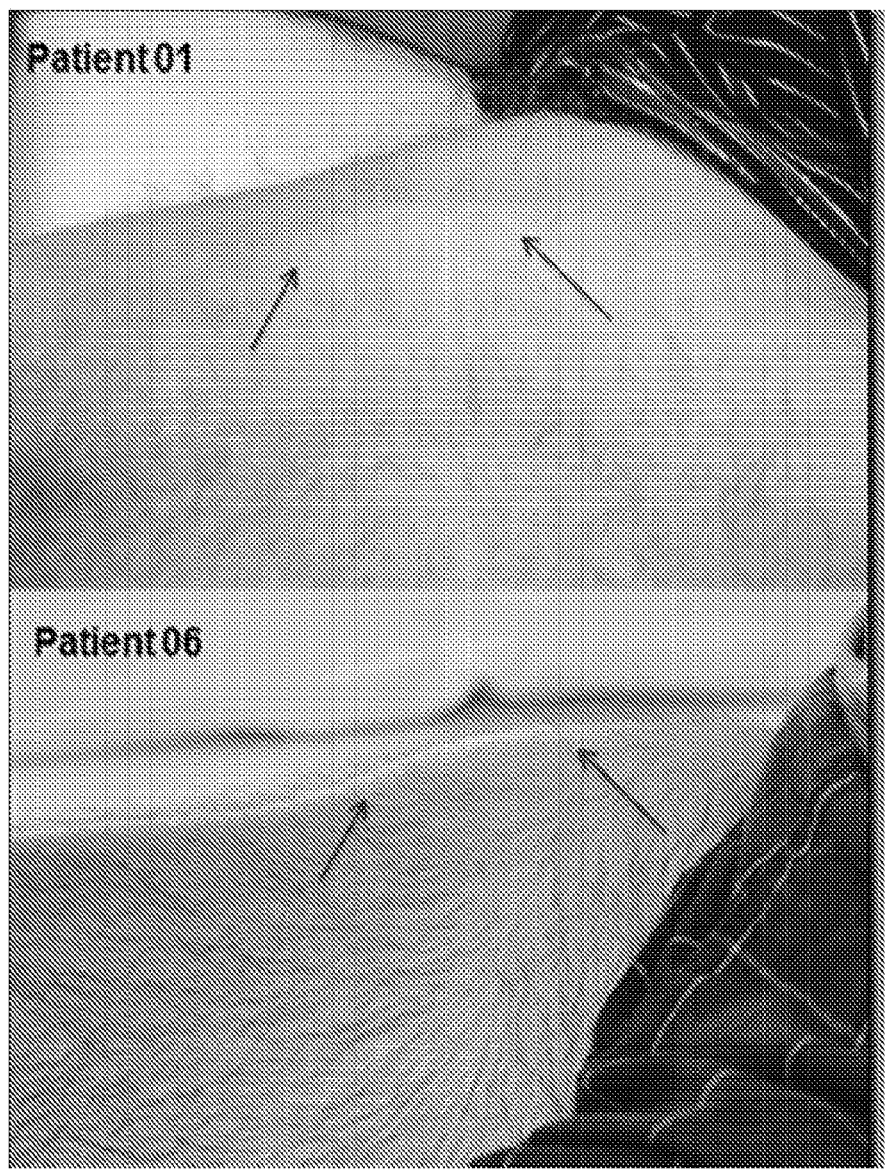
FIG. 5. Focal areas of clinical muscle hypertrophy. Following gene transfer, focal areas of muscle hypertrophy (red arrows) could be seen clinically, as shown in Subjects 01 and 05. We never observed diffuse quadriceps muscle enlargement as we had seen in pre-clinical studies in the non-human primate.

Our goal at the conceptualization of this clinical trial was to diffusely and symmetrically increase the size of the quadriceps muscle. Muscle hypertrophy was an outcome we had seen in mice and non-human primate studies injected with AV1.CMV.FS344, in a manner that extended well beyond the specific sites of injection18, 19. In the cynomolgus macaque each of the three major muscles of the quadriceps (VL, RF, and VM) received a single injection. Follistatin secretion from transduced muscle at the site of injection reached remote sites. In the clinical trial, we compensated for the larger muscle mass by distributing 4 injections to each of three major muscle groups of the quadriceps. However, despite ultrasound-guided injections designed to target muscle and avoid regions of muscle fibrosis, this was only possible up to a degree. Two subjects with strikingly different degrees of muscle fibrosis illustrate the challenge (FIGS. 3*a-d*) of effectively delivering AAV1.CMV.FS344 to muscle. For example, Subject 06 (FIGS. 3*a*, 3*b*) showed significant improvement in 6MWT (108 m) and had less muscle fibrosis compared to Subject 03 (FIGS. 3*c*, 3*d*) who exhibited no significant improvement in the 6MWT (9 m). Subsequent analysis using an MRI-based grading scale applied to thigh muscles at the time of enrollment confirmed fibrosis as a major obstacle in achieving improved 6MWT (FIG. 4). It is apparent that muscle fibrosis precluded the diffuse follistatin-induced muscle hypertrophy that we had seen in the normal muscle of the non-human primate. Of note, in this clinical trial, gross muscle hypertrophy was focal following gene transfer and could be observed on clinical examination (FIG. 5). These areas of muscle were strikingly apparent and often pointed out by the subjects.

Muscle Biopsy Analysis

Figure 6:
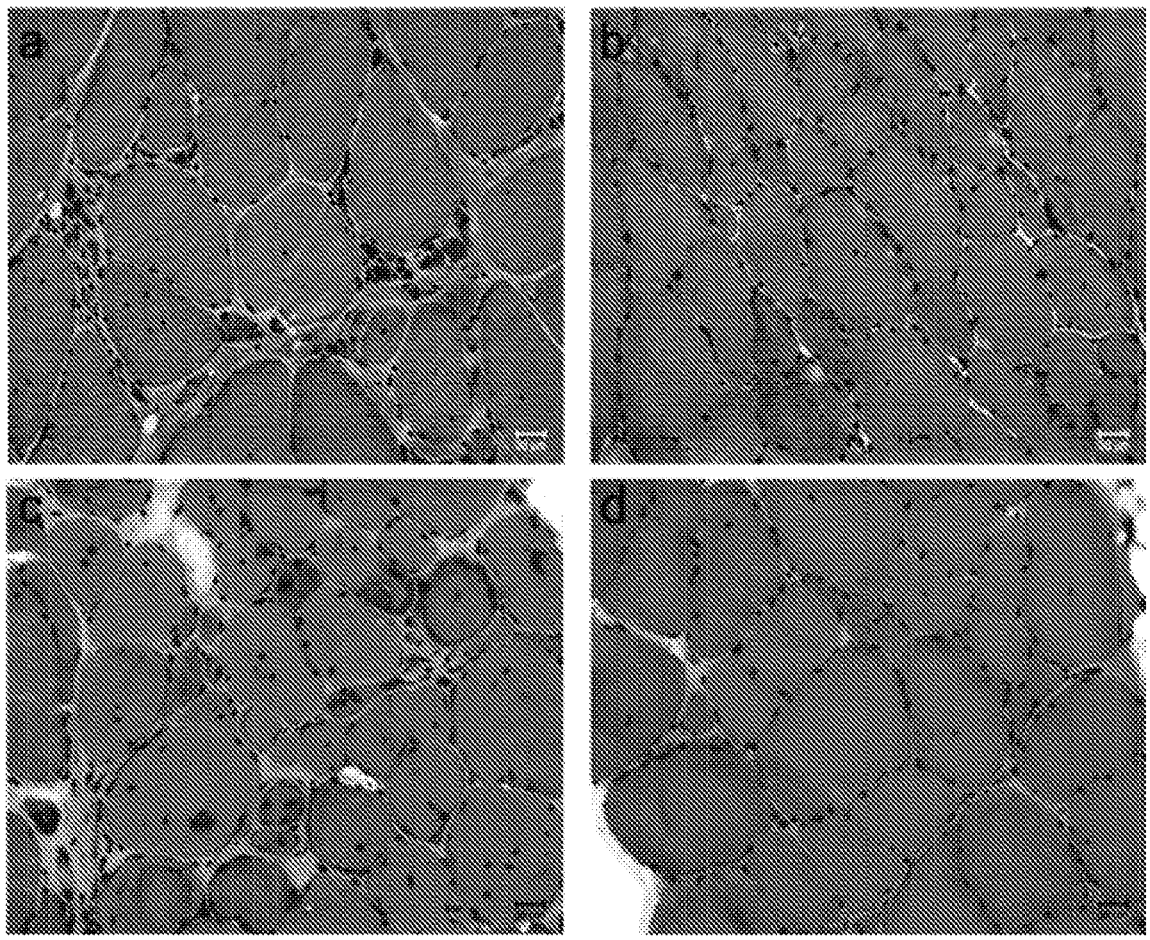
FIG. 6. Muscle biopsy changes following follistatin gene therapy. (a) Pre-treatment biopsy from Subject 05; (b) Post treatment biopsy from Subject 05; (c) Pre-treatment biopsy from Subject 06; (d) Post treatment biopsy from Subject 06. The post-treatment biopsies show reduced fibrosis and a decrease in central nucleation. The number of small muscle fibers is markedly reduced and fewer split fibers are seen. Fiber size analyses showed a shift toward larger mean fiber diameter populations: Subject 05, pre-biopsy 40.14±2.10 µm (n=323 fibers) vs post-biopsy 59.33±1.54 µm (n=292 fibers); p<0.0001; Subject 06, pre 47.48±2.00 µm (n=245 fibers) vs post 63.74±2.45 µm (n=277) p<0.0001.
Figure 7:
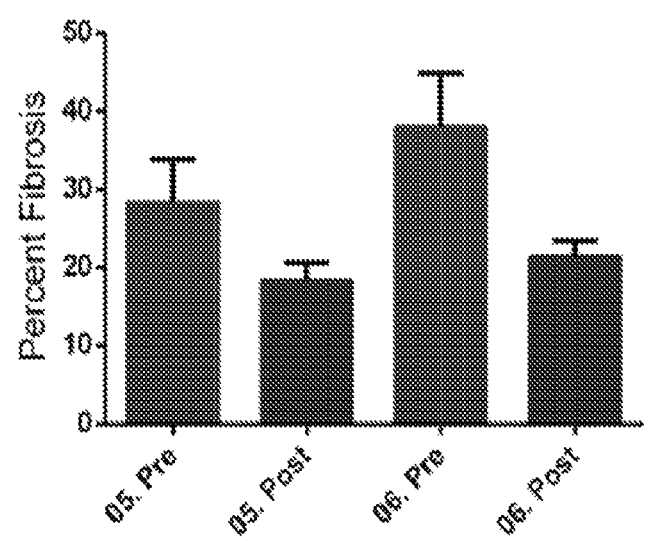
FIG. 7. Reduced fibrosis following follistatin gene therapy. Percent fibrosis using picrosirius staining was quantified comparing pre- and post-treatment muscle biopsies in high dose Cohort. The error bars represent standard error of the mean. Post treatment, we found that fibrosis was reduced to 35% of baseline for Subject 05 and to 43% of baseline for subject 06 (p<0.017; mean percent fibrosis in cohort 2 pre-treatment 33.14±4.47 vs post treatment 19.28±1.73; one-way ANOVA).
Figure 9:
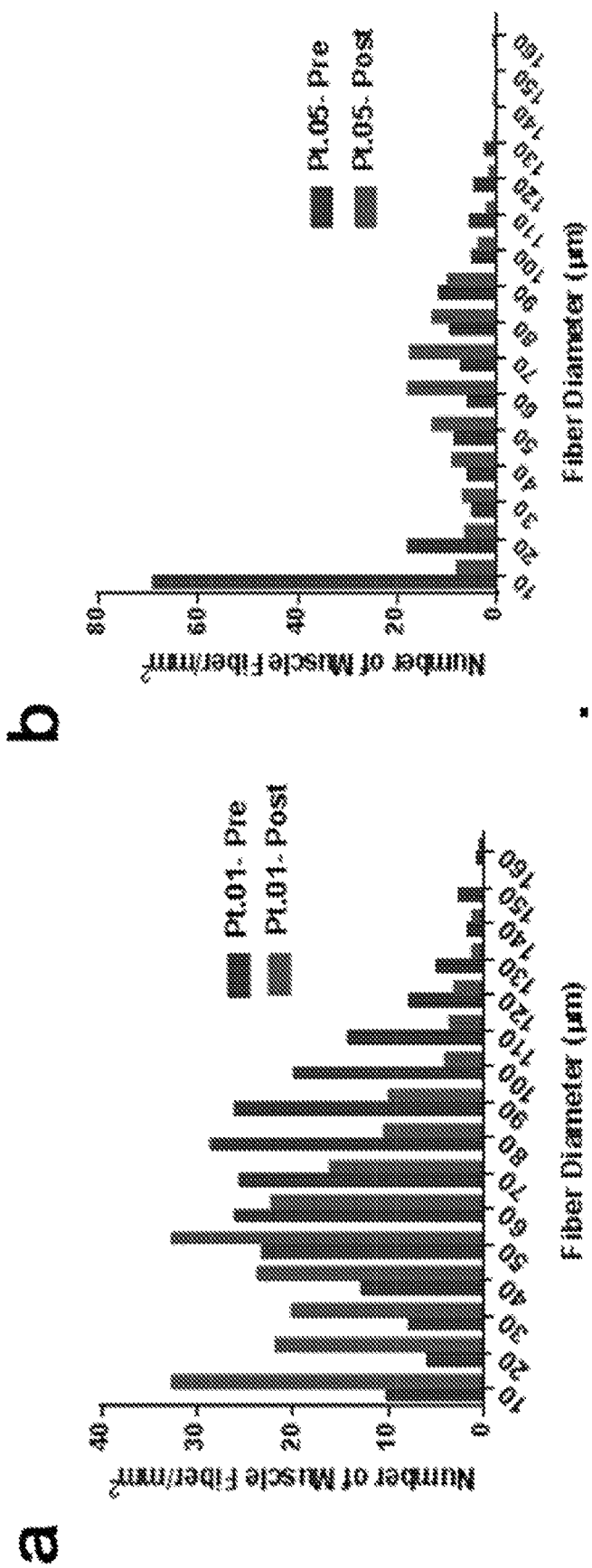
FIG. 9. Muscle fiber size distribution histograms from pre and post treatment biopsies. (a) Post treatment histogram from Pt.01 shows an increase in the number of fibers with diameters between 10 and 50 µm per mm$^2$ area. (b) The pre treatment biopsy from Pt.05 shows a marked increase of severely atrophic round fibers (also see FIG. 6a) and abnormally hypertrophic fibers. (c) A more normalized Poisson-like fiber size distribution with a shift to larger fibers with 40 to 80 µm range is seen with treatment. Decease in abnormally small fibers with treatment is seen in Pt.06 (d) For comparison, normal fiber size distribution from a normal control biopsy.
Figure 9:
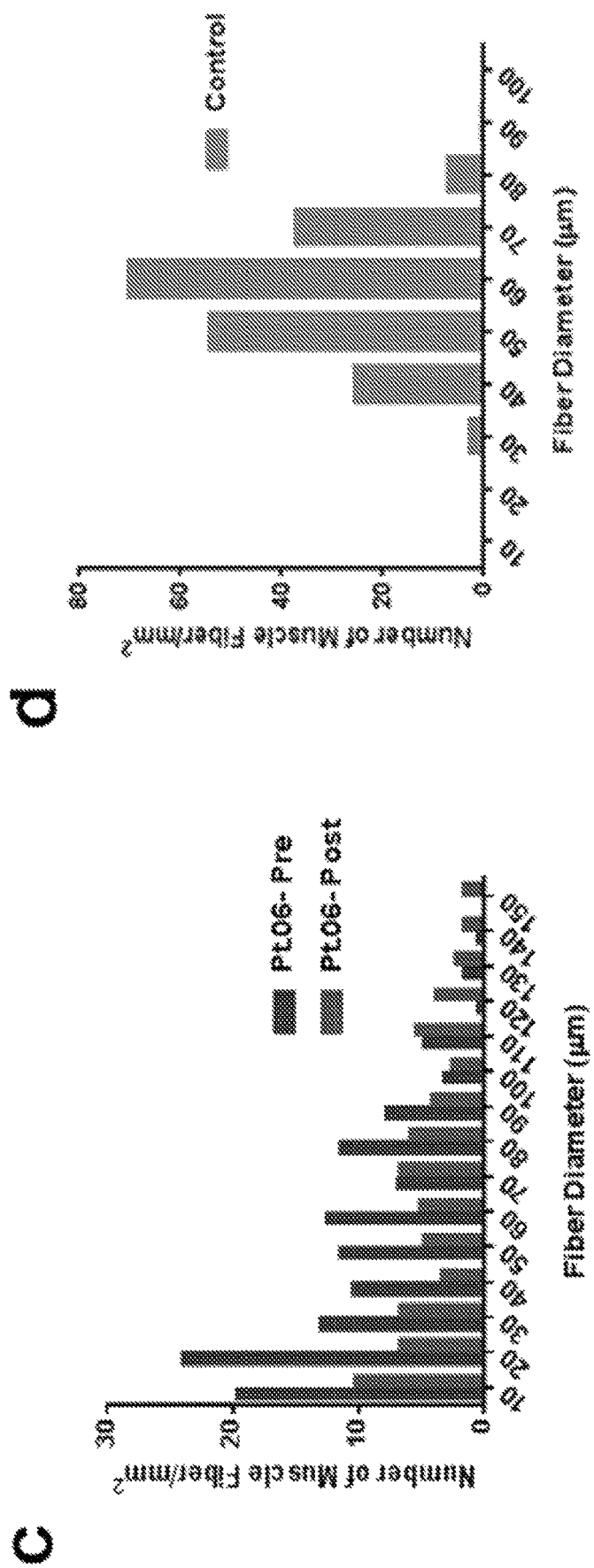
Figure 10:
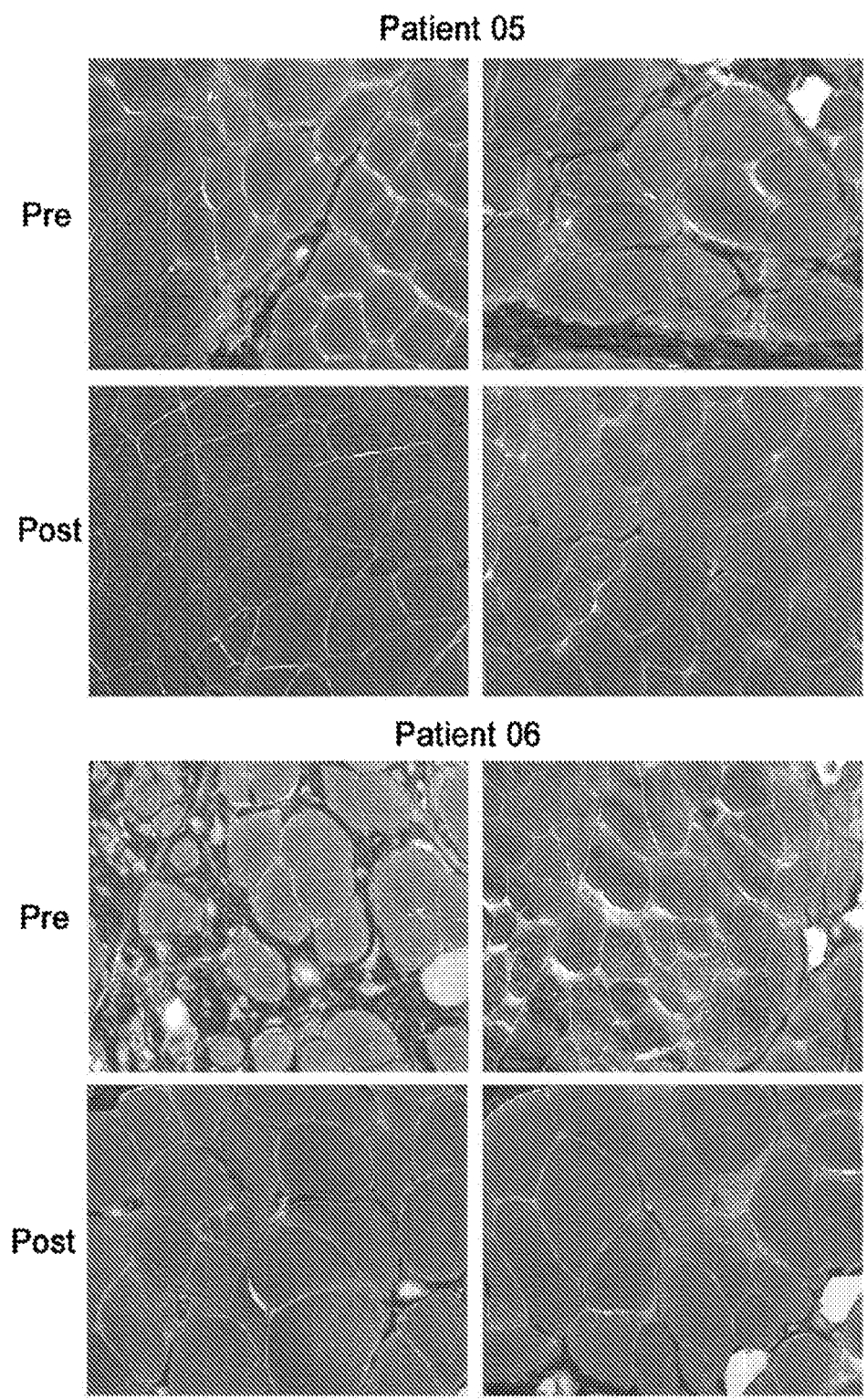
FIG. 10. Picrosirius red collagen staining of muscle pre- and post-follistatin treatment. In post-treatment muscle biopsies, collagen deposition was reduced by FS344 gene therapy (quantified in FIG. 7).
Figure 11:
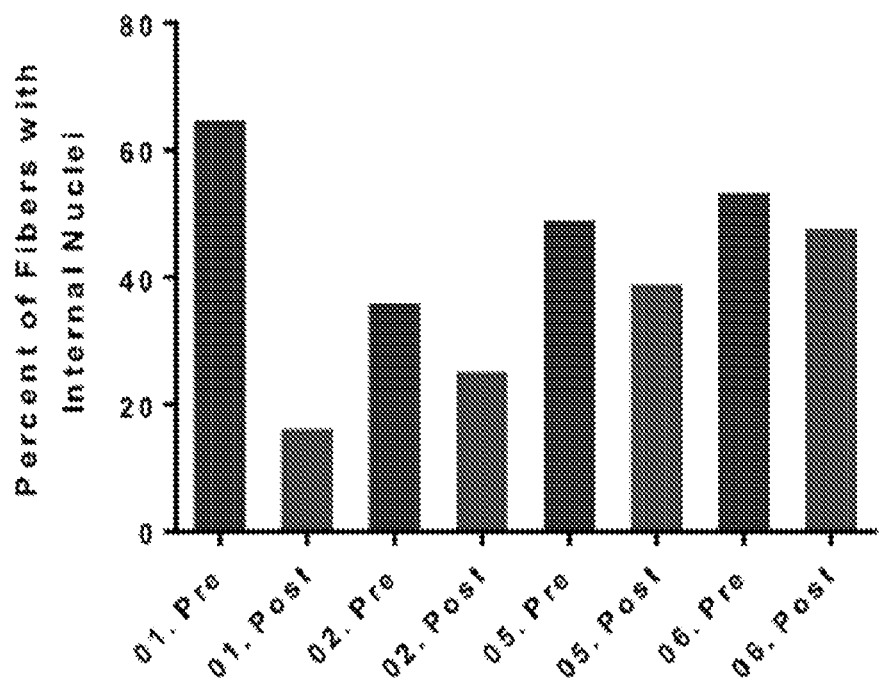
FIG. 11. Follistatin gene therapy and central nucleation. Pre- and post-treatment comparisons show percent of fibers with central nuclei was reduced following FS344 gene delivery.
Figure 12:
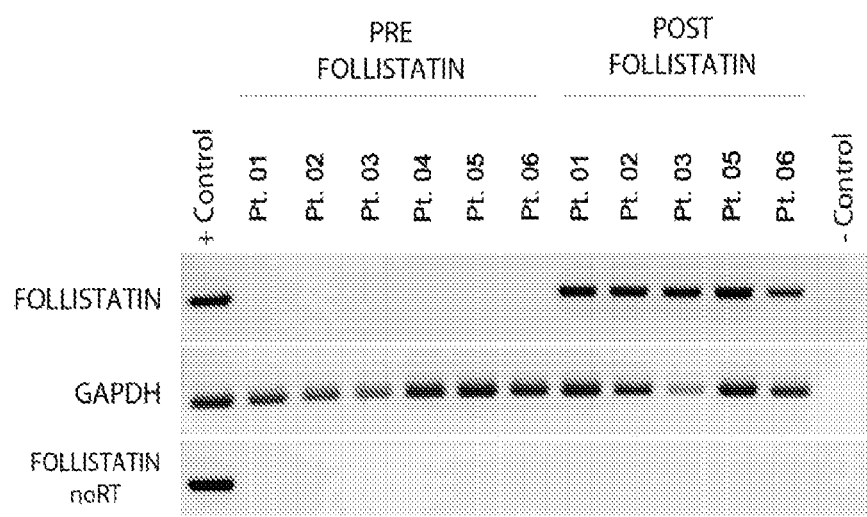
FIG. 12. Pre- and post-treatment RT-PCR on muscle biopsies. There is well-defined follistatin expression specific for FS344 isoform in post treatment muscle biopsies that is not present pre-treatment. Subject 04 had only a pre-treatment muscle biopsy.

To further evaluate the effects of AAV1.CMV.FS344, we performed muscle biopsy analyses comparing pre- and post-treatment muscle biopsies obtained 30 days prior to gene delivery and at 6 months following gene transfer. One subject refused a second biopsy (Subject 04) and another showed severe fibrosis in the area targeted for the second biopsy (Subject 03) limiting interpretation. Post-injection biopsies from the low dose subjects (Cohort 1; Subject 01 and 02) highlighted follistatin-induced regeneration[31-33]. The biopsies demonstrated an increase in the number of muscle fibers per unit area, inclusive of small and medium size diameter subpopulations (FIG. 9*a*). The findings favor improved radial growth of small fibers resulting from enhanced muscle regeneration combined with decreased frequency of necrosis/regeneration cycles in the muscle. The follistatin effect was better defined in the post-injection muscle biopsies from the high dose subjects (Cohort 2, Subject 05 and 06) (FIGS. 6*a-d*; FIGS. 9*b,c*). There was a shift to a larger mean fiber diameter population: Subject 05, pre-biopsy 40.14±2.10 μm (n=323 fibers) vs post-biopsy 59.33±1.54 μm (n=292 fibers); p<0.0001; Subject 06, pre 47.48±2.00 μm (n=245 fibers) vs post 63.74±2.45 μm (n=277) p<0.0001. Post-treatment muscle fibers appeared to be more uniform in size distribution distinct from untreated Becker muscle where many small and hypertrophied fibers are seen side-by-side (FIGS. 6*a,c*). More notable, the quantification of endomysial connective tissue (fibrosis) using picrosirius staining confirmed the anti-fibrotic effect of follistatin previously reported muscle[33,] lung[34], liver[35], and pancreas[36]. We found that the connective tissue was significantly decreased in post treatment biopsy samples from all subjects (p<0.0002, one-way analysis of variance followed by Bartlett's test). In cohort 2 subjects post treatment, we found that connective tissue was reduced to 35% of baseline for Subject 05 and to 43% of baseline for subject 06 (p<0.017, one-way ANOVA) (FIG. 7, FIG. 10). In addition, following gene transfer both cohorts showed a decrease in the percent of fibers with central nuclei (FIG. 11) suggesting that myonuclei movements toward periphery were completed. DNA copy number at the site of biopsy was determined for each subject undergoing post treatment. Muscle transgene expression specific for the FS344 isoform by RT-PCR was corroborated comparing pre- and post treatment muscle biopsies (FIG. 12).

Figure 13:
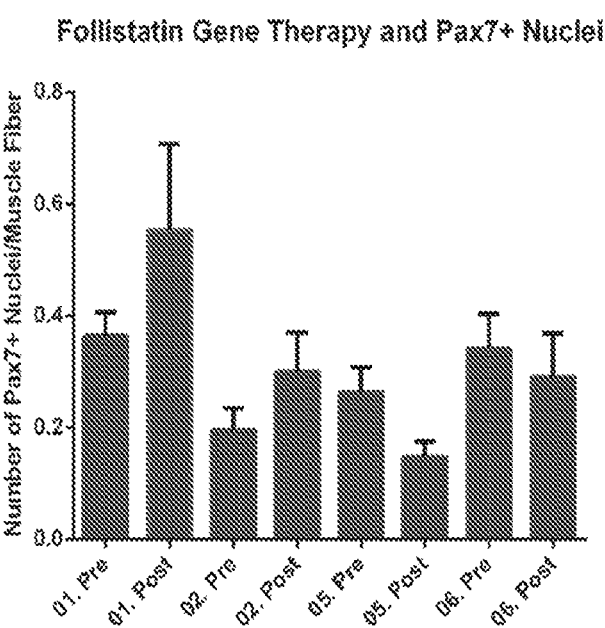
FIG. 13. Pax7 positive nuclei per muscle fiber in pre- and post-treatment biopsies for Subjects 01, 02, 05 and 06. The findings refute concerns that follistatin expression reduces the number of Pax7+satellite cell nuclei.

A potential interesting finding in this study was the number of Pax7+ satellite cell nuclei between pre- and post-gene therapy biopsies. There has been ongoing concern raised by several investigators regarding myostatin inhibition and relation to satellite cell depletion[37-39]. In this study comparing pre- and post-follistatin biopsies there was no consistent decline in the number of Pax7+ satellite cell nuclei per muscle fiber (FIG. 13) and the quantification of Pax7+ satellite cell nuclei post gene transfer consistently exceeded our previously reported control numbers (0.065±0.006)[40].

Expression of MicroRNAs in Response to Follistatin

Figure 14:
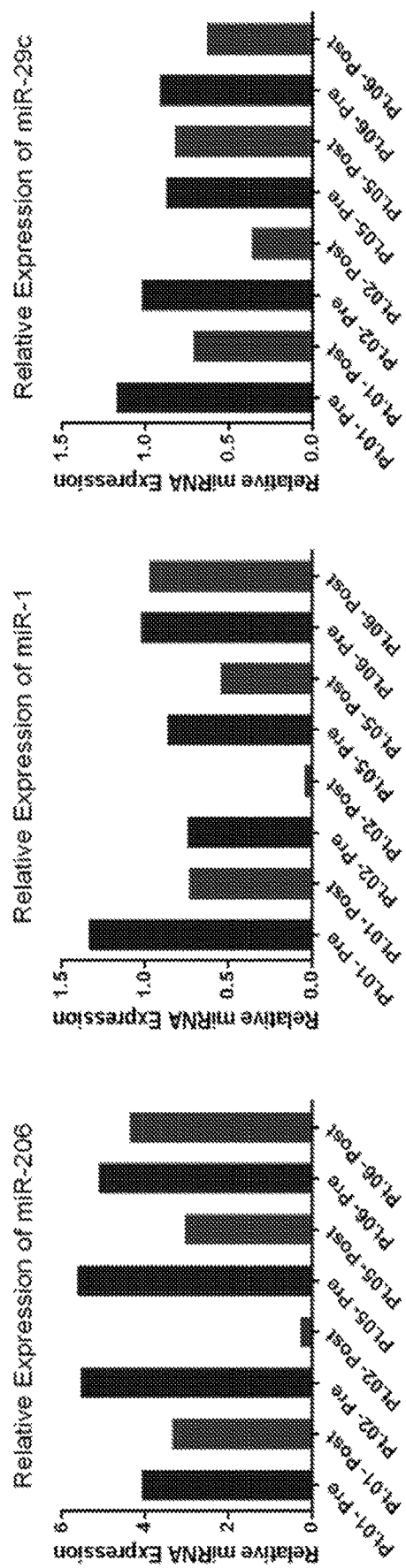
FIG. 14. miR-206, miR-1, and miR29c levels in pre- and post-treatment muscle biopsies for Subjects 01, 02, 05 and 06. The down-regulation of miRs was observed following gene transfer serving as additional biomarker confirming follistatin expression in skeletal muscle.

Previous studies have shown that AAV encoding follistatin reduces expression of miR-206, miR-1, and miR-29a[41]. As a confirmatory biomarker for a follistatin effect, we compared miR-206 expression levels between first and second muscle biopsies from both cohorts following AAV1.CMV.FS344 injection. In BMD muscle, in which perpetual necrosis/regeneration cycles take place, the baseline miR-206 levels were found 4 to 5.6 fold higher than control muscle samples (FIG. 14a). Six months-post gene injections there was a down regulation of miR-206 expression in all subjects suggesting an overall slower rate of necrosis/regeneration events. Similar trends of down regulation of miR-1 and miR-29c were observed in post treatment samples (FIGS. 14b,c).

Discussion

A solid rationale preceded our clinical trial of follistatin gene delivery for BMD. A compelling justification is the lack of treatment for this form of muscular dystrophy including failed trials of glucocorticoids[17], creatine monophosphate[42], sildenafil[15] and an attempt to replace dystrophin using a plasmid-based gene replacement strategy[43]. The motivation for employing an inhibitor of the myostatin pathway originated from both pre-clinical and clinical studies. The potential importance of this pathway was first illustrated in 1997 in the myostatin knock out mouse showing a large and widespread increase in skeletal muscle mass[44]. Myostatin, a member of the transforming growth factor-β superfamily, is an endogenous inhibitor of muscle growth. The effect of myostatin is conserved throughout mammalian species[45-48], including humans where the identification of myostatin gene mutations led to hypermuscularity through the combination of muscle fiber hyperplasia and hypertrophy[49,50]. The benefits of loss of myostatin activity are also well established in dystrophic mice[51-53]. The results of the first clinical trial of myostatin inhibition using a recombinant neutralizing antibody to inhibit myostatin (MYO-029) are likewise of interest showing a small, dose-related increase in muscle mass preferentially targeting BMD subjects in preference to other forms of dystrophy including limb girdle and facioscapulohumeral muscular dystrophies. However, no direct clinical benefit in muscle strength or function was seen in the MYO-029 trial[54].

Follistatin is a potent inhibitor of the myostatin pathway and transgenic mice overexpressing follistatin demonstrate striking increases in muscle mass[55]. The potential for follistatin as a therapeutic vehicle is enhanced because of its independence from the myostatin pathway. In the myostatin-null mouse, follistatin transgene expression results in an impressive quadrupling of muscle mass[20]. In moving to a clinical trial, defining the follistatin isoform with the least off-target toxicity was an important step. The choice was between two isoforms generated by alternative splicing. The FS344 variant includes a C-terminal acidic region that undergoes peptide cleavage to generate the serum circulating, non-tissue binding, FS315 isoform. This isoform avoids off-target effects especially affecting sites within the pituitary-gonadal axis[56-59]. Our initial gene transfer experiments using AAV1.CMV.FS344 in the mdx mouse demonstrated enhanced muscle mass and strength for more than 2 years without adverse effects[18]. We extended these studies to non-human primates for up to 15 months without histologic or functional adverse events to any key organ systems[19].

The intramuscular injection of AAV1.CMV.FS344 to BMD subjects in this clinical trial represents a successful proof-of-principle study with an excellent safety profile that mirrored pre-clinical findings. The major clinical finding is the improvement in the distance walked on the 6MWT following injection of the quadriceps muscles. There was no apparent difference in functional outcome between low and high dose, with two of three subjects improving in each cohort. Impressively, two subjects improved by over 100 m in 6MWT. Two other subjects improved, with increases of 58 m and 29 m. Two subjects failed to significantly improve. We believe that the greatest obstacle to gene expression-related improvement was muscle fibrosis (FIGS. 3 and 4). Whereas in the normal muscle of non-human primates, FS344 led to diffuse muscle enhancement[19], in BMD subjects with underlying widespread connective tissue replacement of muscle, there were only focal areas of muscle hypertrophy (FIG. 5). Thus, future enrollment will benefit from pre-treatment MRI assessment and MRI-guided gene transfer. The extension of that finding is to avoid diffuse fibrosis by early intervention. Having said that, we did find an anti-fibrotic effect in endomysial fibrosis in regions of the biopsy where gene expression was apparent supported by findings including a reduced number of central nuclei, an increased in the number of muscle fibers, and a shift toward larger fiber diameters and more uniform fiber distribution especially in high dose subjects. Overall these findings are consistent with follistatin-induced enhancement of muscle differentiation leading to more efficient regenerative activity[31]. We also found reduced expression of miR-206 and muscle expression of the specific follistatin isoform expressed following AAV gene transfer. We did not find a predictive correlation with DMD gene mutations (Table 1) or with dystrophin expression on muscle biopsy prior to treatment (data not shown).

Figure 8:
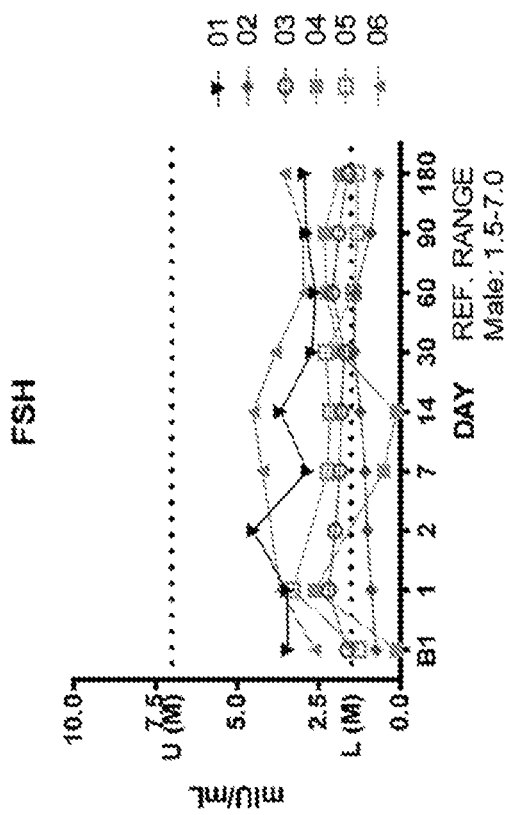
FIG. 8. Hormonal profile for follistatin-treated subjects. Follicle stimulating hormone (FSH), Luteinizing Hormone (LH), Testosterone, and Estrogen levels are shown for each of the subjects in the trial over 180 days.
Figure 8:
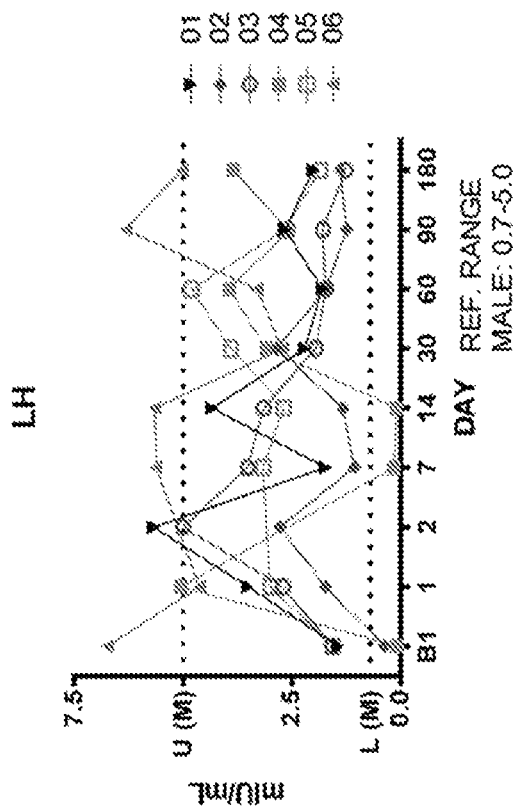
Figure 8:
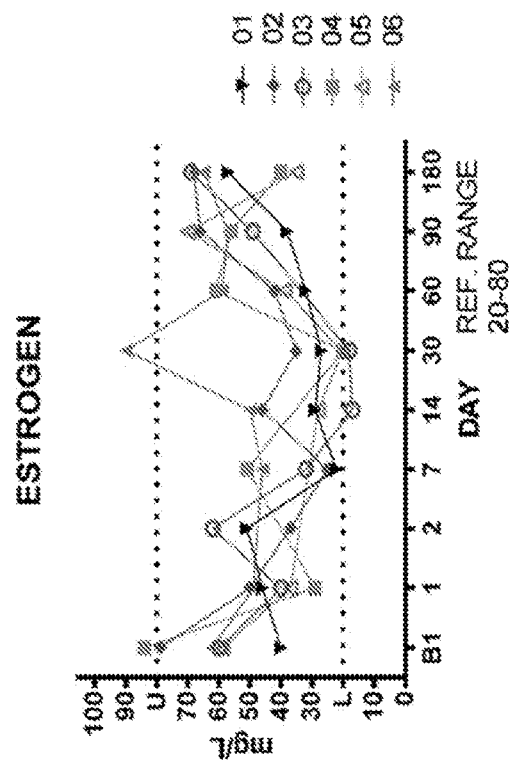
Figure 8:
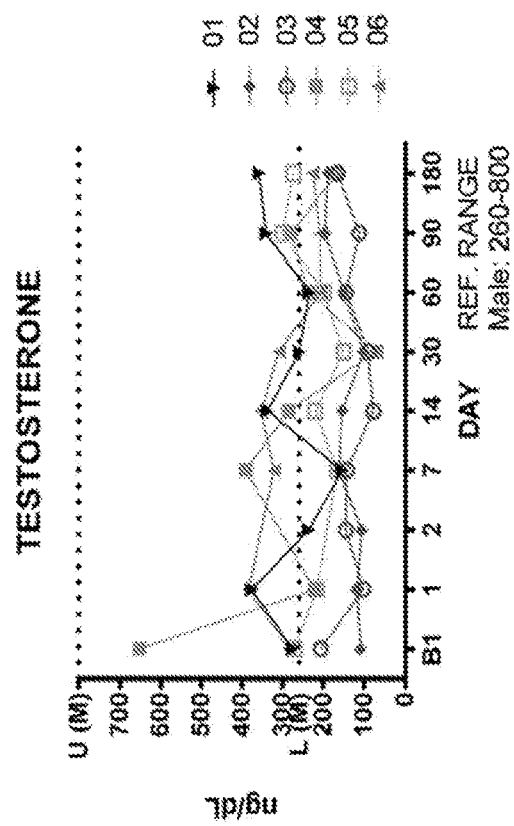

In preparation for this clinical trial safety concerns were raised regarding follistatin dysregulation of pituitary gonadotropins, especially follicle-stimulating hormone (FSH) and luteinizing hormone (LH)[57-59]. FSH and LH are involved in control of the reproductive function in vertebrates. In addition, follistatin is found in gonads and pituitary tissues and autocrine/paracrine effects on gonadotropins effects could be exerted by overexpression of follistatin in these tissues. Data generated from pre-clinical studies in non-human primates showed no changes in FSH, LH, testosterone or estrogen[19]. This safety profile extended to the clinical trial where we again saw no changes in gonadotropins, testosterone or estrogen levels following gene therapy (FIG. 8). In addition, subjects in this clinical trial were closely monitored for a wide range of toxicity in every organ system and no abnormalities were encountered. Follistatin gene therapy delivered by AAV1 under the control of a CMV promoter proved to be exceptionally safe.

The safety findings in combination with gene expression in muscle, and functional improvement provide a firm foundation for application of AAV1.FS344 gene delivery for other musculoskeletal diseases.

Treatment of sporadic inclusion body myositis (sIBM) with intramuscular AAV1.CMV.FS344 is contemplated. In the past, this has been a challenging disease because of lack of available treatment, a long-term debilitating course, and an inflammatory infiltration in muscle that responds poorly to immune suppression. The ability of follistatin to target inflammatory cells, promote muscle regeneration, and increase muscle fiber size, provide significant potential for a therapeutic effect in sIBM. After pre-treatment MRI assessment, IBM subjects were treated by MRI-guided AAV gene transfer by im injection in a single limb of a dose of 2e11 vg/kg/quad, by im injection bilaterally with a dose of 6e11 vg/kg/quad (divided among 12 injection sites) or by im injection bilaterally with a dose of 6e11 vg/kg/quad (divided among 14 injection sites).

Treatment of DMD subjects with intramuscular AAV1.CMV.FS344 changing the protocol to include a wider delivery of vector to multiple muscle groups is also contemplated. After pre-treatment MRI assessment, DMD subjects were treated by MRI-guided AAV gene transfer by im injection bilaterally with a dose of 1e12 vg/kg/limb (divided among 18 injection sites in quadriceps, gluteal and tibialis anterior muscles in each limb). It is also noteworthy for future consideration that dual vector delivery of AAV carrying FS344 in combination with micro-dystrophin in mdx mice improved tetanic force and provided full protection against eccentric contraction[60].

In conclusion, the safety and efficacy as determined by the distance walked in the 6MWT, along with improved muscle histopathology in a first in human clinical trial of AAV1.CMV.FS344 supports studies in other forms of musculoskeletal diseases such as a muscular dystrophy. This study also sets the stage for a pivotal clinical trial for BMD subjects.

SUMMARY

Becker muscular dystrophy (BMD) is a variant of dystrophin deficiency resulting from DMD gene mutations. Phenotype is variable with loss of ambulation in late teenage or late mid-life years. There is currently no treatment for this condition. In this BMD proof-of-principle clinical trial, a potent myostatin antagonist, follistatin (FS), was used to inhibit the myostatin pathway. Extensive pre-clinical studies, using adeno-associated virus (AAV) to deliver follistatin, demonstrated an increase in strength. For this trial, we used the alternatively spliced FS344 to avoid potential binding to off target sites. AAV1.CMV.FS344 was delivered to 6 BMD subjects by direct bilateral intramuscular quadriceps injections. Cohort 1 included 3 subjects receiving $3 \times 10^{11}$ vg/kg/leg. The distance walked on the 6MWT was the primary outcome measure. Subjects 01 and 02 improved 58 meters (m) and 125 meters, respectively. Subject 03 showed no change. In Cohort 2, Subjects 05 and 06 received $6 \times 10^{11}$ vg/kg/leg with improved 6MWT by 108 m and 29 m, whereas, Subject 04 showed no improvement. No adverse effects were encountered. Histological changes corroborated benefit showing reduced endomysial fibrosis, reduced central nucleation, more normal fiber size distribution with muscle hypertrophy, especially at high dose. The results support treatment of musculoskeletal diseases and muscle wasting.

Materials and Methods

Study Subjects

Subject eligibility included proof of BMD mutation, knee extensor weakness 2 standard deviation below normal24, ambulatory, ability to cooperate for testing, willingness to practice contraception during the study, and no evidence of cardiomyopathy, diabetes, or organ system abnormalities of bone marrow, liver, or kidney. Human immunodeficiency virus infection, hepatitis A, B, or C, or known autoimmune diseases were exclusion criteria. IRB approved consent forms were obtained by the principal investigator (JRM) and signed by subjects. Consents included approval for muscle biopsies performed under local anesthesia with incisions made over the proximal vastus lateralis. A randomization table determined the side of the pre-treatment biopsy. The post gene transfer biopsy was done at 6 months post gene transfer to the same muscle of the opposite extremity with particular effort to stay within the area of the gene injection sites. Taking immunosuppressive drugs other than glucocorticoids during the trial was prohibited. The Institutional Review Board at Nationwide Children's Hospital approved this clinical trial. The protocol followed the *Helsinki Declaration*; all subjects gave their written informed consent and the trial was registered at Clin.Trials.Gov.

Vector Production, Purification and Characterization

Figure 15:
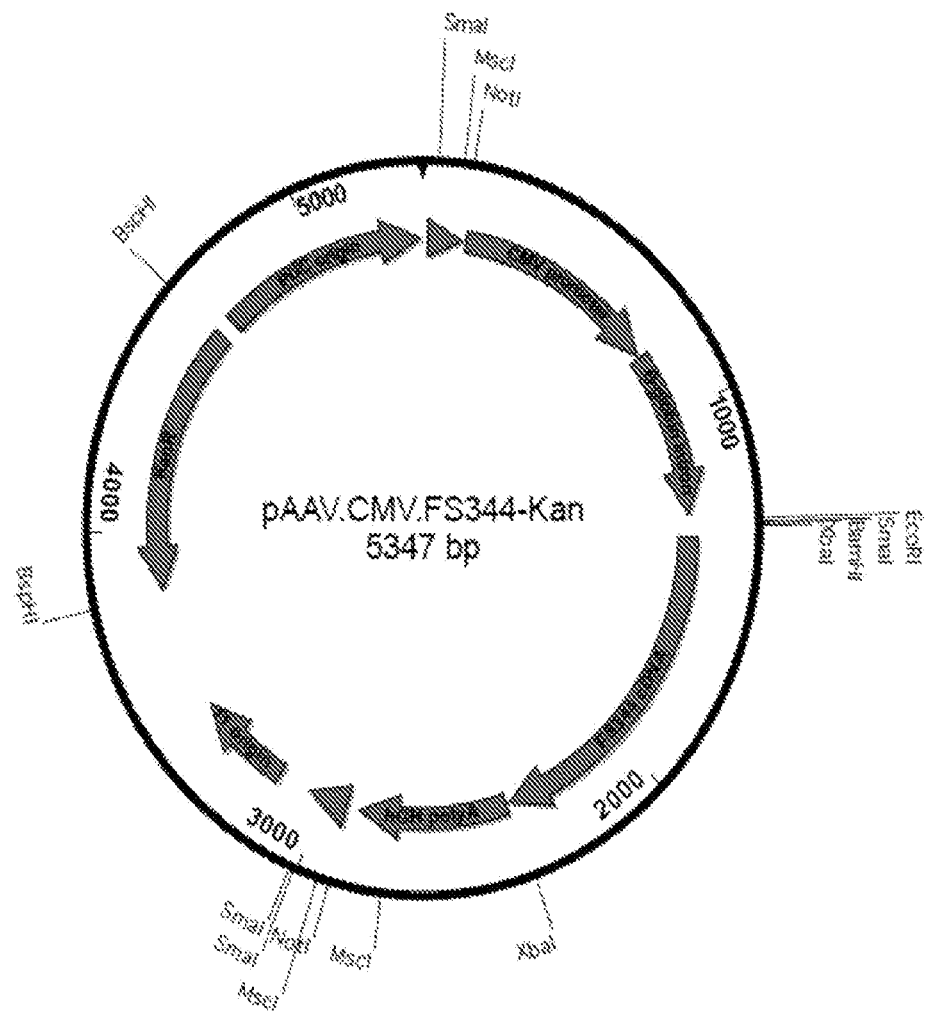
FIG. 15. AAV.CMV.FS344-Kan plasmid used for vector production. The orientation and placement sites are shown in relation to restriction sites. The human follistatin gene expression cassette FS344 cDNA is flanked by AAV2 inverted terminal repeats (ITRs). The CMV immediate early promoter/enhancer used the β-globin intron. The plasmid contains the kanamycin resistance gene.

The AAV1 vector product was produced using the AAV vector plasmid pAAV.CMV.FS344-Kan (FIG. 15). It contains the human follistatin gene expression cassette flanked by AAV2 inverted terminal repeat sequences (ITR). It is this sequence that was encapsidated into AAV1 virions. The plasmid was constructed by inserting the human follistatin cDNA sequence (human cDNA, Genbank Accession # NM 013409) obtained from Origene Technologies (Rockville, Md.) into plasmid pAAV-MCS (Stratagene, La Jolla, Calif.) using BamH I and Xho 1 restriction sites. The construct contains the CMV immediate early promoter/enhancer and uses the β-globin intron for high-level expression and the human growth hormone polyadenylation termination signal. Subsequently, the bla open reading frame encoding ampicillin resistance was removed using BspH I digestion and the kanamycin resistance gene (amino-glycoside 3'-phosphotransferase II gene) from Transposon Tn5 was PCR amplified with BspH I ends from plasmid pSELECT-neo-mcs (InVivogen, San Diego, Calif.) and used to replace the bla gene to yield the AAV vector plasmid pAAV.CMV.FS344-Kan (5,347 bp). The only viral sequences in this vector are the inverted terminal repeats of AAV2, which are required for both viral DNA replication and packaging of the rAAV vector genome. All plasmids used in the production process were produced by Aldevron Inc. under its GMP-S™ quality system and infrastructure utilizing the most salient features of cGMP manufacturing; traceability, document control, and materials segregation. rAAV1.CMV.FS344 was produced in the Nationwide Children's Viral Vector GMP Manufacturing Facility. Vector production followed previously published methods using plasmid DNA tri-transfection of HEK293 cells followed by iodixanol and anion exchange column chromatography purification[25]. Briefly, cells were cultivated in ten-tray Corning Cell Stacks, and all open manipulations were performed in class II biosafety cabinets in an ISO Class 5 environment. The purification process was performed in a closed system; where possible however, iodixanol gradient purification, an open step, was performed in an ISO Class 5 BSC. Purification consisted of collecting the cells plus media and subjecting them to a single pass microfluidization at 1000 psig followed by clarification and tangential flow filtration for volume reduction, iodixanol gradient purification and anion exchange chromatography on the 40% iodixanol fraction. After purification, the product was diafiltered with final formulation buffer and sterile filtered to yield the two Purified Bulks. After Purified Bulk testing, the two Purified Bulks were pooled, diluted with sterile formulation buffer (20 mM Tris pH 8.0, 1 mM $MgCl_2$, 200 mM NaCl, 0.001% Pluronic F68) and a manual Final Fill was performed within a BSC in the CMF Purification Room. Following Fill, the drug product underwent release testing in anticipation of formal release by our Quality Assurance Unit (QAU). Tests were performed on In-Process samples, the Purified Bulk Drug Substance, and the Final Fill drug product along with stability testing. Certificates of Stability and Analysis were submitted and approved by the FDA. The DNase Resistant Particle titer (also referred to as vector genomes [vg]) were determined for In-Process, Purified Bulk and Release Testing samples using real-time quantitative PCR (qPCR) using serial dilutions of a plasmid standard (pAAV.CMV.FS344-Kan) by the NCH-CMF QC laboratory and

```
CMV Forward Primer
5'-TGGAAATCCCCGTGAGTCAA-3',    (SEQ ID NO: 2)

CMV Reverse Primer
5'-CATGGTGATGCGGTTTTG.G-3',    (SEQ ID NO: 3)
and

CMV probe FAM-
CCGCTATCCACGCCCATTGATG-FAM.    (SEQ ID NO: 4)
```

Functional Measures

The primary functional outcome, the 6MWT was performed at Nationwide Children's Hospital by the same clinical evaluators (L.P.L. and L.A.). The 6MWT was assessed at baseline prior to the muscle biopsy. Single-day assessments were performed at 30 days, 60 days, 90 days, 6 months and 1 year. Direct measure of maximum voluntary isometric contraction of quadriceps muscles (knee extension) served as a secondary outcome measure. These outcome measures have been previously described[29].

Muscle Biopsy Analysis

Biopsies were obtained from the quadriceps muscles, mounted in gum tragacanth and frozen in isopentane cooled in liquid nitrogen. A standard battery of stains including H&E, modified Gomori trichrome, and ATPase (pH 4.2, 4.6, and 9.4) was performed pre- and post-treatment. H&E stained cross sections were used for fiber size measurements and internal nuclei determinations. Depending on the available tissue size, 8-12 randomly selected areas were photographed at 20× and stored. Fiber diameters were recorded with a calibrated micrometer, using the AxioVision, 4.2 software (Zeiss). Fiber size distribution histograms were generated as number per mm$^2$ area. These same images were used to identify the number of fibers with either one or more central nuclei and percent of fibers with central nuclei. The amount of endomysial and perimysial connective tissue was quantified in pre- and post-treatment biopsies using the Picro Sirius Red Stain Kit (Abcam ab150681). Twelve fields were randomly selected in pre- and post-treatment biopsies and photographed at 20×; the level of fibrosis was analyzed with ImagePro software. Analysis was made using customs method with 2.5 minute counter stained slides without color correction. Red area (as proportion of fibrotic area) was expressed as percent of total area. The mean±SE of the number of images represented each biopsy. Pax7 positive satellite cells were identified with mouse Pax7 IgG1 antibody (R & D systems) by immunohistochemistry protocol of Super Sensitive polymer-HRP detection kit using i6000™ Automated Staining System from Biogenex®. Briefly, cryosections were fixed in 2% paraformaldehyde for 10 min at 4° C. and incubated in Pax7 antibody (1:100 dilutions) for 30 min after blocking with peroxide and Power Block™ for 10 min. Slides were washed 5 times with IHC Supersensitive™ wash buffer. Finally, 3,3'-Diaminobenzidine (DAB) was used as a substrate and Mayor's hematoxylin as a counterstain. Pax7 positive nuclei counts were done using ImageScope® software (Apereo) and expressed as number of Pax7 positive nuclei per muscle fiber.

In pre-treatment biopsies, immunohistochemistry was performed to correlate dystrophin expression with outcome measures. The number of dystrophin positive fibers (NCL-Dys2, Novacastra Laboratories) and quantification of dystrophin intensity were performed using Bioquant image analysis Software™ (Nashville, Tenn.). RT-PCR was used to confirm expression of follistatin transcript derived from the AAV.CMV.FS344 vector. RNA was isolated from pre and post treatment biopsies and following cDNA conversion, a vector specific PCR product was amplified using the following primers: forward primer 5'-CGAACATCGATTGAATTCCC-3' (SEQ ID NO: 5) and reverse primer 5'-CTTGCTCAGTTCGGTCTT-3' (SEQ ID NO: 6). To ensure specificity for amplification of vector derived transcript, the forward primer was designed to be complementary to an unspliced and transcribed region in the distal 3' region of the CMV promoter with the reverse primer binding to the follistatin transgene.

Quantitative PCR to Detect Genome Copy Number

Taqman qPCR was used to quantify the number of vector genome copies compared to baseline biopsies as previously described 26, 27. A vector specific primer probe was used to determine the copy number, reported as vector genomes per microgram of genomic DNA. The primer sets amplified a unique sequence of the CMV promoter within the CMV.FS cassette: 5-TGGAAATCCCCGTGAGTCAA-3 (SEQ ID NO: 7); a CMV reverse primer, 5-ATGGTGATGCG-GTTTTGG-3 (SEQ ID NO: 8); and CMV probe, 5-FAM-CCGCTATCCACGCCCATTGATG-TAMRA-3 (IDT) (SEQ ID NO: 9).

Identification of Muscle Specific MicroRNA Expression

Total RNA was isolated from the specimens using mirVana miRNA isolation kit (Life Technologies®). Reverse transcription was performed by using Taqman microRNA reverse transcription kit (Applied Biosystems®). Quantitative reverse transcription-polymerase chain reaction (qRT-PCR) for miR-1, miR-206, miR-133a and U6 snRNA was performed using RT kits from Life Technologies® specific for each miR. The catalog numbers for each as follows, miR-1: 4427975, ID 002222, miR-206: 4427975, ID 000510, miR-29c: 4427975, ID000587, U6: 4427975, ID001973. Each miRNA expression was normalized to U6 snRNA expression. Expression data is shown as means of relative expression values obtained from three samples and normalized to normal control levels (set at 1). Standard error of means and presented in a graph format.

IFN-γ ELISpot Analysis

ELISpot (enzyme-linked immunospot) assays were performed on fresh PBMCs, which were added at a concentration of 2×10$^5$/well in duplicate wells of a 96-well flat-bottom membrane-plate (Millipore, Billerica, Mass.). Three peptide pools were used for the AAV1capsid protein (Genemed Synthesis, Inc.), containing 34-36 peptides, each 18 amino acids long and overlapping by 11 residues. Two peptide pools encompassing the follistatin protein (Genemed Synthesis, Inc.) were used as previously described[18], Concanavalin A (Sigma) served as a positive control, and 0.25% DMSO as a negative control. Peptides were added directly to the wells at a final concentration of 1 μg/mL in 200 μL of AIM-HS (Aim-V lymphocyte media [Invitrogen] supplemented with 2% human AB serum [Gemini-BioScience BLCL medium (RPMI 1640 [Gibco] supplemented with 10% fetal bovine serum [Gibco] and Pen Strep [Gibco]). Human IFN-γ ELISpot kits were purchased from U-CyTech (Utrecht, Netherlands). After the addition of PBMCs and peptides, the plates were incubated at 37° C. for 48 hours and then developed according to the manufacturer's protocol. IFN-γ-spot formation was counted using a Cellular Technologies Limited Systems analyzer (CTL, Cleveland, Ohio).

Anti-AAV Neutralizing Antibody Titers

The assay is based on the ability of neutralizing antibody (Nab) in serum to block target cell transduction with a B-gal reporter vector stock. C12 rep expressing HeLa cells (Viral Vector Core, Nationwide Children's Hospital) were plated in a 96-well plate (Corning) at a concentration of 5e4 cells/well, Plates were incubated at 37° C. with 5% CO$_2$. The following day, an aliquot of subject serum was heat inactivated for 30 minutes at 56° C. Serum was diluted in duplicate 2-fold with DMEM in a 96-well plate so that the plate contained 1:50-1:1638400 dilutions. 5e7 DRP/ml AAV 1.CMV.βgal virus was added to the serially diluted wells in a volume of 25 μl. For the assay cutoff, 25 μl of 5e7, 1e7, and 5e6 DRP/ml were added to other wells containing 1:50 diluted naïve serum The 96-well plates were then rocked for 2-5 minutes, and incubated for 1 hour at 37° C. Media was then removed and all 50 μl of the diluted serum/AAV1 complexes were added to the corresponding well containing C12 cells. 50 μl of the Ad5 (MOI=250) were added to the diluted serum samples. After overnight incubation at 37° C., the media was replaced with 10% FBS DMEM media the media was removed after 36 hr. of incubation and gently washed with 200 μl/well of PBS (Invitrogen). 100 μl/well of Pierce β-gal Assay Reagent (Thermo Scientific) were added and incubated for 30 minutes at 37° C. The plates were then read at 405 nm on a SPECTRA max M2 plate reader (Molecular Devices). The 5e6 DRP/ml positive control was the assay cutoff, which represents an equivalent of 10% infection and 90% neutralization. The farthest serum dilution producing an average absorbance at 405 nm that was less than the average absorbance of the 5e6

DRP/ml positive control was considered the anti-AAV1 titer.

Anti-Follistatin Antibody Titers

An ELISA (Enzyme-Linked Immunosorbent Assay) was performed to measure the level of circulating anti-follistatin antibody in plasma. Briefly, Immulon-4 96-well plates (ISC BioExpress) were coated with 100 μL of human follistatin protein in carbonate buffer (pH 9.4; Pierce) per well. Plates were sealed overnight at 4° C. Plates were blocked with 280 μL per well of a 5% nonfat dry milk and 1% normal goat serum (Invitrogen) in PBS for 3 hours at 25° C. Subject plasma was diluted at a 1:50 ratio in solution identical to the blocking solution and 100 μL added in duplicate to both wells coated with follistatin in carbonate buffer and wells coated with carbonate buffer alone. Plates were incubated at 25° C. for 1 hour before being washed five times with 280 μL of PBS-T (0.05% Tween). Blocking solution was used again to dilute the secondary antibody, goat anti-human IgG-HRP (Sigma) at a 1:10,000 dilution. Wells received 250 μL of the secondary antibody and were incubated at 25° C. for 30 minutes before being washed 5 times and blotted dry. Tetramethybenzidine (TMB; 100 μL/well; Pierce) was added and incubated at 25° C. for 10 minutes in the dark, before the addition of 100 μL of 1N H2S04 (Acros Organics) to stop the reaction. The absorbance at 450 Å was measured using a Wallace 1420-050 Multilabel Counter (Perkin Elmer). Samples were considered positive if the absorbance at 450 Å average of the antigen-coated wells was three times greater than wells coated with carbonate buffer alone.

Muscle Imaging

Muscle MRI was performed using T1 weighted spin echo on a 3.0 Tesla GE Signa Excite (General Electric Healthcare; Milwaukee, Wis.). Noncontrast enhanced images obtained from both legs were collected at baseline and six months post-gene therapy treatment for all six subjects. Axial T1-weighted images of the lower extremities to the knees were obtained to study pelvic and thigh musculature. A body coil was used for obtaining T1 spin echo pulse sequences (repetition time [TR] 650 msec; echo time [TE] 15 msec) with a 256×256 matrix and a slice thickness of 10 mm each with no gap between slices. A field of view (FOV) of 480 mm was used and a total of 48 slices for each leg was obtained. A retrospective analysis of the images was performed by applying a semi-quantitative method for grading the degree of individual muscle involvement[61-63]. Grading of muscles was based on the following scoring system.

Stage 0: Normal appearance
Stage 1: Scattered small areas of increased intensity
Stage 2a: Numerous discrete areas of increased intensity less than 30% of the volume of the muscle
Stage 2b: Numerous discrete areas of increased intensity with early confluence, 30%-60% of the volume of the muscle
Stage 3: Washed-out appearance due to confluent areas increased intensity with muscle still present at the periphery
Stage 4: End-stage appearance, muscle entirely replaced by areas of increased intensity Analysis of degree of muscle involvement on MRI using the above described scoring system was performed by two independent observers (S.A. and A.G.) and a consensus on the scoring was reached for all muscle groups in all six subjects. Individual muscles were graded separately with the exception of the vastus lateralis and intermedius that were graded as one muscle due to poorly differentiated boundaries.

Statistical Analyses

GraphPad Prism software (La Jolla, Calif.) was used for all statistical analyses. For all comparisons two-tailed Student's t test was used or where appropriate One Way ANOVA was applied. A value of $P<0.05$ was considered statistically significant.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

DOCUMENT CITATIONS

1. England, S B, Nicholson, L V, Johnson, M A, Forrest, S M, Love, D R, Zubrzycka-Gaarn E E, et al. (1990). Very mild muscular dystrophy associated with the deletion of 46% of dystrophin. *Nature* 343:180-182.
2. Nigro, G, Muntoni, F. (1997). 42nd ENMC Sponsored International Workshop: X-linked cardiomyopathies. 21-23 Jun. 1996, Naarden, The Netherlands. *Neuromuscul Disord* 7:397-403.
3. Bushby, K M, Gardner-Medwin D, Nicholson, L V, Johnson, M A, Haggerty, I D, Cleghorn, N J, et al. (1993). The clinical, genetic and dystrophin characteristics of Becker muscular dystrophy. II. Correlation of phenotype with genetic and protein abnormalities. *J Neurol* 240:105-112.
4. Beggs, A H, Hoffman, E P, Snyder, J R, Arahata K, Spect L, Shapiro, F, et al. (1991). Exploring the molecular basis for variability among subjects with Becker muscular dystrophy: dystrophin gene and protein studies. *Am J Hum Genet* 49:54-67.
5. Aartsma-Rus, A, Fokkema, I, Verschuuren, J, Ginjaar, L, van Deutekom, J, van Ommen G-J, et al. (2009). Theoretic applicability of antisense-mediated exon skipping for Duchenne muscular dystrophy mutations. *Hum Mutat* 30:293-299.
6. Flanigan, K M, Dunn, D M, von Niederhausern, A, Soltanzadeh, P, Gappmaier, E, Howard M T, et al. (2009). Mutational spectrum of DMD mutations in dystrophinopathy subjects: application of modern diagnostic techniques to a large cohort. *Hum Mutat* 30:1657-1656

7. Flanigan, K M, Dunn, D M, von Niederhausern, A, Soltanzadeh, P, E, Howard, M T, Sampson, J B, et al. (2011). Nonsense mutation-associated Becker muscular dystrophy: interplay between exon definition and splicing regulatory elements within the DMD gene. *Hum Mutat* 32:299-308.
8. van den Bergen, J C, Wokke, B H, Janson A A, van Duinen, S G, Hulsker, M A, Ginjaar, H B, et al. (2014). Dystrophin levels and clinical severity in Becker muscular dystrophy subjects. *J Neurol Neurosurg Psychiatry* 85:747-53.
9. Neri, M, Torelli, S, Brown, S, Ugo, I, Sabatelli, P, Merlini, L, et al. (2007). Dystrophin levels as low as 30% are sufficient to avoid muscular dystrophy in the human. *Neuromuscul Disord* 17:913-918.
10. Brooke, M H, Fenichel, G M, Griggs, R C, Mendell, J R, Moxely, R, Miller, J P, Province, M A. (1983). Clinical investigation in Duchenne Dystrophy. II. Determination of the "power" of therapeutic trials based on the natural history. *Muscle Nerve* 6: 91-103.
11. Bushby, K M D, Gardner-Medwin, D. (1993). The clinical, genetic and dystrophin characteristics of Becker muscular dystrophy. I. Natural History. *J Neurol* 240:98-104.
12. Mendell, J R, Province, M A, Moxley, R T, Griggs, R C, Brooke, M H, Fenichel, G M, et al. (1987). Clinical investigation of Duchenne muscular dystrophy. A methodology for therapeutic trials based on natural history controls. *Arch Neurol* 44, 808-811.
13. von Mitzlaff, H C, Liechti-Gallati, S, Rosler, K M, Burgunder, J M. (1993). Quadriceps myopathy as dystrophin-associated myopathy. *Schweiz Med Wochenschr* 123:1865-1869.
14. Sunohara, N, Arahata, K, Hoffman, E P, Yamada, H, Nishimiya J, Arikawa, E, et al. (1990). Quadriceps myopathy: forme fruste of Becker muscular dystrophy. *Ann Neurol* 28:634-639.
15. Witting, N, Kruuse, C, Nyhuus, B, Prahm, K, Citirak, G, Lundgaard, S, et al. (2014). Effect of sildenafil on skeletal and cardiac muscle in Becker muscular dystrophy. *Ann Neurol July* 4 Epub ahead of print.
16. Leung, D G, Herzka, D A, Thompson, W R, He, B, Bibat, G, Tennekoon, G, et al. (2014). Sildenafil does not improve cardiomyopathy in Duchenne/Becker muscular dystrophy. *Ann Neurol July* 4 Epub ahead of print.
17. Backman E, Henriksson K G. (1995). Low-dose prednisolone treatment in Duchenne and Becker muscular dystrophy. *Neuromuscul Disord* 5:233-241.
18. Haidet, A M, Rizo, L, Handy C, Umapathi, P, Eagle, A, Shilling, C, et al. (2008). Long-term enhancement of skeletal muscle mass and strength by single gene administration of myostatin inhibitors. *Proc Natl Acad Sci USA* 105:4318-4322.
19. Kota, J, Handy, C R, Haidet, A M, Montgomery, C L, Eagle, A, Rodino-Klapac, L R, et al. (2009). Follistatin Gene Delivery Enhances Muscle Growth and Strength in Nonhuman Primates. *Sci Transl Med* 1:6ra15.
20. Lee S J. (2007). Quadrupling muscle mass in mice by targeting TGF-beta signaling pathways. PLoS ONE 2:e789.
21. Inouye S, Guo, Y, DePaolo, Y, Shimonaka, M, Ling, N, Shimasaki, S. (1991). Recombinant expression of human follistatin with 315 and 288 amino acids: Chemical and biological comparison with native porcine follistatin. *Endocrinology* 129:815-822.
22. Sugino, K, Kurosawa, N, Nakamura, T, Takio, K, Shimasaki, S, Ling, N, et al. (1993). Molecular heterogeneity of follistatin, an activin-binding protein: Higher affinity of the carboxyl-terminal truncated forms for heparan sulfate proteoglycans on the ovarian granulosa cell. *J Biol Chem* 268:15579-15587.
23. Nakatani, M, Takehara, Y, Sugino, H, Matsumoto, M, Hasegawa, Y, Murakami, T, et al. (2008). Transgenic expression of a myostatin inhibitor derived from follistatin increases skeletal muscle mass and ameliorates dystrophic pathology in mdx mice. *FASEB J* 22:477-487.
24. Tawil, R, McDermott, M P, Mendell, J R, Kissel, J, Griggs, R C. (1994). Facioscapulohumeral muscular dystrophy (FSHD): design of natural history study and results of baseline testing. FSH-DY Group. *Neurology* 44: 442-446.
25. Nathwani A C, Tuddenham E G, Rangarajan S, Rosales C, McIntosh J, Linch D C, et al. (2011). Adenovirus-associated virus vector-mediated gene transfer in hemophilia B. *N Engl J Med* 365: 2357-65.
26. Mendell, J R, Rodino-Klapac, L R, Rosales-Quintero, Coley B D, Galloway G, Lewis S, et al. (2010). Sustained Alpha-Sarcoglycan Gene Expression after Gene Transfer in Limb-Girdle Muscular Dystrophy, Type 2D. *Ann Neurol* 68:629-638.
27. Mendell, J R, Rodino-Klapac, L R, Rosales-Quintero, X, Kota J, Coley, B D, Galloway G, et al. (2009). LGMD2D gene therapy restores alpha-sarcoglycan and associated proteins. *Ann Neurol* 66:290-297.
28. Viollet, L, Gailey, S, Thornton, D J, Friedman, N, Flanigan, K M, Mahan, J D, Mendell J R. (2009). Utility of Cystatin C to monitor renal function in Duchenne muscular dystrophy. *Muscle Nerve* 40:438-42.
29. Mendell J R, Rodino-Klapac L R, Sahenk Z, Roush K, Bird L, Lowes L P, et al. (2013). Eteplirsen for the treatment of Duchenne muscular dystrophy. *Ann Neurol* 74:637-647
30. McDonald C M, Henricson E K, Abresch R T, Florence J M, Eagle M, Gappmaier E, et al. (2013). THE 6-minute walk test and other endpoints in Duchenne muscular dystrophy: Longitudinal natural history observations over 48 weeks from a multicenter study. *Muscle Nerve* 48:343-356.
31. Yaden, B C, Croy, J E, Wang, Y, Wilson, J M, Datta-Mannan, A, Sheltler, P, et al. (2014). Follistatin: a novel therapeutic for the improvement of muscle regeneration. *J Pharmacol Exp Ther* 349:355-371.
32. McCroskery, S, Thomas, M, Platt, L, Hennebry, A, Nishimura, T, McLeay, L, et al. (2005). Improved muscle healing through enhanced regeneration and reduce fibrosis in myostatin null mice. *J Cell Sci* 118:3531-3541.
33. Zhu J, Li Y, Lu A, Gharaibeh B, Ma J, Kobayashi T, Quintero A J, et al. (2011). Follistatin improves skeletal muscle healing after injury and disease through an interaction with muscle regeneration, angiogenesis, and fibrosis. *Am J Pathol.*179:915-30.
34. Aoki, F, Kurabayashi, M, Hasegawa, Y, Kojima, I. (2005). Attenuation of bleomycin-induced pulmonary fibrosis by follistatin. *Am J Respir Crit Care Med* 172: 713-720.
35. Patella, S, Phillips, D J, Tchongue, J, de Kretser, D M, Sievert, W. (2006). Follistatin attenuates early liver fibrosis: effects on hepatic stellate cell activation and hepatocyte apoptosis. *Am J Physiol Gastrointest Liver Physiol* 290:G137-144
36. Ohnishi, N, Miyata, T, Ohnishi, H, Yasuda, H, Tamada, K, Ueda, N, Mashima, H, Sugano K. (2003). Activin A is an autocrine activator of rat pancreatic stellate cells: potential therapeutic role of follistatin for pancreatic fibrosis. *Gut* 52:1487-1493.
37. Lee, S-J, Huynh, T V, Lee, Y-S, Sebald, S M, Wilcox-Adelman, S A, Iwamori, N, et al. (2012). Role of satellite cells versus myofibers in muscle hypertrophy induced by inhibition of the myostatin/activin signaling pathway. *Proc Natl Acad Sci USA* E2353-E2360.
38. McCroskery, S, Thomas, M, Maxwell, L, Sharma, M, Kambadur, R. (2003). Myostatin negatively regulates satellite cell activation and self-renewal. *J Cell Biol* 162:1135-1147.
39. Gilson, H, Schakman, O, Kallista, S, Lause, P, Tsuchida, K, Thissen, J P. (2009). Follistatin induces muscle hypertrophy through satellite cell proliferation and inhibition of both myostatin and activin. *Am J Physiol Endocrinol Metab* 297:E157-E164.
40. Rosales, X Q, Malik, V, Sneh, A, Chen, L, Lewis, S, Kota, J, et al. (2013). Impaired regeneration in LGMD 2A supported by increased Pax7 positive satellite cell content and muscle specific microRNA dysregulation. *Muscle Nerve* 47:731-739
41. Winbanks C E, Beyer C, Hagg A, Qian H, Sepulveda P V, Gregorevic P. (2013). miR-206 represses hypertrophy of myogenic cells but not muscle fibers via inhibition of HDAC4. *PLoS One.* 8:e73589.
42. Walter, M C, Lochmuller, H, Reilich, P, Klopstock, T, Huber, R, Hartard, M, et al. (2000). Creatine monohydrate in muscular dystrophies: A double-blind placebo-controlled clinical study. *Neurology.* 54:1848-1850.
43. Romero, N, Braun, S, Benveniste, O, leturcq F, Jean-Yves, H, Morris, G E, et al. (2004). Phase I study of dystrophin plasmid-based gene therapy in Duchenne/Becker muscular dystrophy. *Hum Gene Ther.* 15:1065-1076
44. McPherron, A C, Lawler, A M, Lee, S J. (1997). Regulation of skeletal muscle mass in mice by a new TGF-beta superfamily member. *Nature* 387:83-90
45. McPherron, A C, Lee, S J. (1997). Double muscling in cattle due to mutations in the myostatin gene. *Proc Natl Acad Sci USA* 94:12457-12461.
46. Grobet, L, Martin, L J, Poncelet, D, Pirottin, D, Brouwers, B, Riquet, J, et al. (1997). A deletion in the bovine myostatin gene causes the double-muscled phenotype in cattle. *Nat Genet* 17:71-74.
47. Mosher D S, Quignon P, Bustamante C D, Sutter, N B, Mellersh, C S, Parker, H G, et al. (2007). A mutation in the myostatin gene increases muscle mass and enhances racing performance in heterozygote dogs. *PLoS Genetics* 3:779-786
48. Clop, A, eMarcq, F, Takeda, H, Pirottin, D, Tordoir, X, Bibé, B, et al. (2006). A mutation creating a potential illegitimate microRNA target site in the myostatin gene affects muscularity in sheep. *Nature Genet* 38:813-818.
49. Schuelke, M, Wagner, K R, Stolz, L E, Hübner, C, Kömen, W, Braun, T, et al. (2004). Myostatin mutation associated with gross muscle hypertrophy in a child. *N Engl J Med* 350:2682-2688.
50. Pontera, P, Bernardini, L, Stangoni, G, Capalbo, A, Rogaia, D, Ardisia, C, et al. (2009). 2q31.2q32.3 deletion syndrome: report of an adult subject. *Am J Med Genet* 149A:706-712.
51. Bogdanovich S, Krag, T O, Barton, E R, Morris, L D, Whittemore L A, Ahima, R S, Khurana, T S. (2002). Functional improvement of dystrophic muscle by myostatin blockade. *Nature* 420: 418-421.
52. Wagner, K R, McPherron, A C, Winik, N, Lee, S-J. (2002). Loss of myostatin attenuates severity of muscular dystrophy in mdx mice. *Ann Neurol* 52: 832-836.
53. Bogdanovich, S, Perkins, K, Krag, T, Whittemore, L A, Khurana T. (2005). Myostatin propeptide-mediated ameliortion of dystophic pathophysiology. *FASEB J* 19: 543-549.
54. Wagner, K R, Fleckenstein, J L, Amato, A A, Barohn, R J, Bushby, K, Escolar, D M, et al. (2008). A Phase I/II trial of MYO-029 in Adult Subjects with Muscular Dystrophy. *Ann Neurol* 63:561-571.
55. Lee, S-J, McPherron, A C. (2001). Regulation of myostatin activity and muscle growth. *Proc Natl Acad Sci USA* 98: 9306-9311.
56. Chemical and biological comparison with native porcine follistatin. *Endocrinology* 129:815-822.
57. Kaiser, U B, Lee, B L, Carroll, R S, Unabia, G, Chin, W W, Childs, G. V. (1992). Follistatin gene expression in the pituitary: localization in gonadotropes and folliculostellate cells in diestrous rats. *Endocrinology* 130: 3048-3056
58. Michel, U, Albiston, A, Findlay, J K. (1990). Rat follistatin: gonadal and extragonadal expression and evidence for alternative splicing. *Biochem Biophys Res Commun* 173:401-407
59. Aroua, S, Maugars, G, Jeng, S-R, Chang, C-F, Weltzen, F A, Rousseau, K, Dufour, S. (2011). Pituitary gonadotropins FSH and LH are oppositely regulated by the activin/follistatin system in a basal teleost, the eel. *Gen Comp Endocrinol* 175:82-91
60. Rodino-Klapac L R, Janssen P M L, Shontz K M, Canan B, Montgomery C L, Griffin D, et al. (2013). Micro-dystrophin and follistatin co-delivery restores muscle function in aged DMD model. *Hum Mol Genet* 22:4929-4937
61. Hawley R J, Jr., Schellinger D, O'Doherty D S. (1984). Computed tomography patterns of muscles in neuromuscular diseases. *Arch Neurol* 41:383-387.
62. Mercuri E, Talim B, Moghadaszadeh B, Petit N, Brockington M, Counsell S, et al. (2002). Clinical and imaging findings in six cases of congenital muscular dystrophy with rigid spine syndrome linked to chromosome 1p (RSMD1). *Neuromuscul Disord* 12:631-638.
63. Kinali M, Arechavala-Gomeza V, Cirak S, Glover A, Guglieri M, Feng L, et al. (2011). Muscle histology vs MRI in Duchenne muscular dystrophy. *Neurology* 76:346-353.

We claim:

1. A method of improving follistatin-344 gene expression in muscle and thereby increasing muscle fiber number and/or increasing muscle fiber diameter and enhancing muscle function in a subject in need thereof comprising the step of administering to the subject by one or more intramuscular injections a composition comprising infectious encapsidated recombinant adeno-associated viruses (rAAVs), each rAAV comprising a rAAV genome comprising AAV inverted terminal repeats flanking a polynucleotide encoding follistatin-344, wherein the polynucleotide is operatively linked to transcriptional control DNA and wherein the genome lacks AAV rep and cap DNA, and
   wherein the administration is prior to development of diffuse muscle fibrosis in the subject or wherein the intramuscular injection or injections avoid regions of muscle fibrosis in the subject.

2. The method of claim 1 wherein the subject suffers from Becker muscular dystrophy.

3. The method of claim 2, wherein the rAAV dose injected is at least about $6\times10^{11}$ viral genome per kilogram per leg (vg/kg/leg) or at least about $1.2\times10^{12}$ vg/kg/subject.

4. The method of claim 1 wherein the subject suffers from Duchenne muscular dystrophy.

5. The method of claim 4, wherein the rAAV dose injected is at least about $2\times10^{11}$ vg/kg/leg or at least about $6\times10^{11}$ vg/kg/subject.

6. The method of claim 1 wherein the subject suffers from inclusion body myositis.

7. The method of claim 6, wherein the rAAV dose injected is at least about $1.2\times10^{12}$ viral genome per kilogram per limb (vg/kg/limb).

8. The method of claim 1, 2, 3, 4, 5, 6 or 7 wherein the rAAV administered is AAV1.CMV.FS344.

9. The method of claim 1, 2, 3, 4, 5, 6 or 7 wherein the intramuscular injections are guided by magnetic resonance imaging or positron emission tomography.

* * * * *